US009569887B2

(12) United States Patent
Siddiqi et al.

(10) Patent No.: US 9,569,887 B2
(45) Date of Patent: Feb. 14, 2017

(54) METHODS OF MODELLING AND CHARACTERISING HEART FIBER GEOMETRY

(71) Applicant: The Royal Institution for the Advancement of Learning / McGill University, Montreal (CA)

(72) Inventors: Kaleem Siddiqi, Westmount (CA); Emmanuel Piuze-Phaneuf, Montreal (CA); Jon Sporring, Allerod (DK)

(73) Assignee: The Royal Institution for the Advancement of Learning / McGill University, Montreal (CA)

( * ) Notice: Subject to any disclaimer, the term of this patent is extended or adjusted under 35 U.S.C. 154(b) by 0 days.

(21) Appl. No.: 14/712,236

(22) Filed: May 14, 2015

(65) Prior Publication Data
US 2015/0332483 A1   Nov. 19, 2015

Related U.S. Application Data

(60) Provisional application No. 61/993,600, filed on May 15, 2014.

(51) Int. Cl.
*G06T 17/00*   (2006.01)
*G06T 11/00*   (2006.01)
(Continued)

(52) U.S. Cl.
CPC ............. *G06T 17/00* (2013.01); *A61B 5/0044* (2013.01); *A61B 6/504* (2013.01); *G06T 7/0038* (2013.01);
(Continued)

(58) Field of Classification Search
CPC ........ G06T 17/00; G06T 11/003; G06T 17/30; G06T 15/205; G06T 7/0065; G06T 15/08; G06T 7/0038; G06T 2210/41; G06T 2207/20182; G06T 2207/10092; G06T 2215/06; G06T 2207/20164; G06T 2207/30048; G06T 15/00; G06T 17/20; G06T 19/00; A61B 5/0044; A61B 6/504
See application file for complete search history.

(56) References Cited

U.S. PATENT DOCUMENTS 5,151,856 A * 9/1992 Halmann ................ G06T 15/00
                                                    600/410
5,435,310 A * 7/1995 Sheehan ................ B82Y 15/00
                                                    382/128
(Continued)

OTHER PUBLICATIONS

Dillen F (1992) Ruled submanifolds of finite type. Proc Am Math Soc 114:795-798.
(Continued)

*Primary Examiner* — Manav Seth
(74) *Attorney, Agent, or Firm* — Norton Rose Fulbright Canada LLP

(57) ABSTRACT

The identification and determination of aspects of the construction of a patient's heart is important for cardiologists and cardiac surgeons in the diagnosis, analysis, treatment, and management of cardiac patients. For example minimally invasive heart surgery demands knowledge of heart geometry, heart fiber orientation, etc. While medical imaging has advanced significantly the accurate three dimensional (3D) rendering from a series of imaging slices remains a critical step in the planning and execution of patient treatment. Embodiments of the invention construct using diffuse MRI data 3D renderings from iterating connections forms derived from arbitrary smooth frame fields to not only corroborate biological measurements of heart fiber orientation but also provide novel biological views in respect of heart fiber orientation etc.

18 Claims, 15 Drawing Sheets

(51) Int. Cl.
    *G06T 7/00*      (2006.01)
    *G06T 15/08*     (2011.01)
    *G06T 15/20*     (2011.01)
    *G06T 17/30*     (2006.01)
    *G06T 15/00*     (2011.01)
    *G06T 17/20*     (2006.01)
    *G06T 19/00*     (2011.01)
    *A61B 5/00*      (2006.01)
    *A61B 6/00*      (2006.01)
(52) U.S. Cl.
    CPC ........... *G06T 7/0065* (2013.01); *G06T 11/003* (2013.01); *G06T 15/00* (2013.01); *G06T 15/08* (2013.01); *G06T 15/205* (2013.01); *G06T 17/20* (2013.01); *G06T 17/30* (2013.01); *G06T 19/00* (2013.01); *G06T 2207/10092* (2013.01); *G06T 2207/20164* (2013.01); *G06T 2207/20182* (2013.01); *G06T 2207/30048* (2013.01); *G06T 2210/41* (2013.01); *G06T 2215/06* (2013.01)

(56) References Cited

U.S. PATENT DOCUMENTS

| | | | | |
|---|---|---|---|---|
| 5,947,899 | A * | 9/1999 | Winslow | A61B 5/00 128/920 |
| 5,969,524 | A * | 10/1999 | Pierpaoli | G01R 33/56341 324/307 |
| 6,614,226 | B2 * | 9/2003 | Wedeen | A61B 5/055 324/307 |
| 8,095,321 | B2 * | 1/2012 | Hisada | G06F 19/3437 702/19 |
| 2002/0042569 | A1 * | 4/2002 | Wedeen | A61B 5/055 600/411 |
| 2008/0120078 | A1 * | 5/2008 | Hisada | G06T 11/206 703/11 |
| 2009/0131740 | A1 * | 5/2009 | Gharib | A61M 1/1068 600/17 |
| 2014/0088943 | A1 * | 3/2014 | Trayanova | A61B 34/10 703/11 |
| 2016/0061920 | A1 * | 3/2016 | Mekkaoui | A61B 5/055 382/131 |

OTHER PUBLICATIONS

Thas C (1979) Minimal generalized ruled surfaces in the Euclidean space Em. Technical Report, Seminar of Higher Geometry (State University of Ghent, Belgium).
Thas C (1988) A property of the Veronese surface. J Geom 32:157-168.
Nitsche JJ (1989) Lectures on Minimal Surfaces: vol. 1, Introduction, Fundamentals, Geometry and Basic Boundary Value Problems (Cambridge Univ Press, Cambridge, UK).
Osserman R (2002) A Survey of Minimal Surfaces (Dover, Mineola, NY).
Savadjiev P (2009) Perceptual Organisation in Diffusion MRI: Curves and Streamline Flows. PhD thesis (McGill Univ, Montreal), p. 143.
Savadjiev P, Zucker SW, Siddiqi K (2007) On the differential geometry of 3D flow patterns: Generalized helicoids and diffusion MRI analysis. Proceedings of the IEEE 11th international Conference on Computer Vision, 10.1109/ICCV.2007.4409086.
LeGrice IJ, et al. (1995) Laminar structure of the heart: Ventricular myocyte arrangement and connective tissue architecture in the dog. Am J Physiol Heart and Circ Physiol 269:H571-H582.
Nielsen PM, LeGrice IJ, Smaill BH, Hunter PJ (1991) Mathematical model of geometry and fibrous structure of the heart. Am J Physiol Heart and Circ Physiol 260:H1365-1378.

LeGrice IJ, Hunter PJ, Smaill BH (1997) Laminar structure of the heart: A mathematical model. Am J Physiol Heart and Circ Physiol 272:H2466-H2476.
Piuze E, Kry PG, Siddiqi K (2011) Generalized helicoids for modeling hair geometry. Comput Graph Forum 30:247-256.
Hayden Ha (1931) On a generalized helix in a Riemannian n-space. Proc Lond Math Soc s2-32:337-345.
Jones DK, ed. (2010) Diffusion MRI: Theory, Methods, and Applications (Oxford Univ Press, New York).
Chen J, et al. (2005) Regional ventricular wall thickening reflects changes in cardiac fiber and sheet structure during contraction: Quantification with diffusion tensor MRI. Am J Physiol Heart and Circ Physiol 289:H1898-H1907.
Hsu EW, Muzikant AL, Matuievicius SA, Penland RC, Henriquez CS (1998) Magnetic resonance myocardial fiber-orientation mapping with direct histological correlation. Am J Physiol Heart arid Circ Physiol 274:H1627-H1634.
Tseng W-YI,Wedeen VJ, Reese TG, Smith RN, Halpern EF (2003) Diffusion tensor MRI of myocardial fibers and sheets: Correspondence with visible cut-face texture. J Magn Reson Imaging 17:31-42.
Coghlan C, Hoffman J (2006) Leonardo da Vinci's flights of the mind must continue: Cardiac architecture and the fundamental relation of form and function revisited, Eur J Cardiothorac Surg 29(Suppl 1):S4-17.
Fisher RA (1953) Dispersion on a sphere. Proc R Soc London Ser A 217:295-305.
Spotnitz HM (2000) Macro design, structure, arid mechanics of the left ventricle. J Thorac Cadiovasc Surg 119:1053-1077.
Aelen FW, et al. (1997) Relation between torsion and cross-sectional area change in the human left ventricle. J Biomech 30:207-212.
Arts T, Veenstra PC, Reneman RS (1984) Torsion of the left ventricle during the ejection phase in the intact dog. Cardiovasc Res 18:183-193.
Lumens J, Delhaas T, Arts T, Cowan BR, Young AA (2006) Impaired subendocardial contractile myofiber function in asymptomatic aged humans, as detected using MRI. Am J Physiol Heart Circ Physiol 291:H1573-H1579.
Bouligand Y (1972) Twisted fibrous arrangements in biological materials and cholesteric mesophases. Tissue Cell 4:189-217.
Jawad H, Lyon AR; Harding SE, Ali NN, Boccaccini AR (2008) Myocardial tissue engineering. Br Med Bull 87:31-47.
Tseng W-YI, Dou J, Reese TG, Wedeen VJ (2006) Imaging myocardial fiber disarray and intramural strain hypokinesis in hypertrophic cardiomyopathy with MRI. J Magn Reson Imaging 23:1-8.
Strijkers GJ, et al. (2009) Diffusion tensor imaging of left ventricular remodeling in response to myocardial infarction in the mouse. NMR Biomed 22:182-190.
Jones DK; Horsfield MA, Simmons A (1999) Optimal strategies for measuring diffusion in anisotropic systems by magnetic resonance imaging. Magn Res Med 42:515-525.
Borgefors G (1984) Distance transformations in arbitrary dimensions. Comput Vision Graph 27:321-345.
Athanasuleas, C.L., Buckberg, G.D., Stanley, A.W., Siler, W., Dor, V., Di Donato, M., Menicanti, L., De Oliveira, S.A., Beyersdorf, F., Kron, I.L., et al.,: Surgical ventricular restoration in the treatment of congestive heart failure due to post-infarction ventricular dilation. Journal of the American College of Cardiology 44(7), 1439{1445 (2004).
Piuze, E., Lombaert, H., Sporring, J., Siddiqi, K: Cardiac fiber inpainting using cartan forms. In: Medical Image Computing and Computer-Assisted Intervention MICCAI 2013; pp. 509-517. Springer (2013).
Rios, L.M., Sahinidis, N.V.: Derivative-free optimization: A review of algorithms and comparison of software implementations. Journal of Global Optimization 56(3), 1247(1293 (2013).
Sengupta, P.P., Korinek, J., Belohlavek, M., Narula, J., Vannan, M.A., Jahangir, A., Khandheria, B. K.: Left ventricular structure and function: basic science for cardiac imaging. Journal of the American College of Cardiology 48(10), 1988-2001 (2006).
Song, K., Nam, Y.J., Luo, X., Qi, X. Tan, W., Huang, G.N., Acharya, A., Smith, C.L., Tallquist, M.D., Neilson, E.G., et al.: Heart repair

(56) References Cited

OTHER PUBLICATIONS by reprogramming non-myocytes with cardiac transcription factors. Nature 485 (7400), 599-604 (2012).

Streeter, D.D.: Gross morphology and fiber geometry of the heart. In: Berne, R.M., Sperelakis, N. (eds.) Handbook of Physiology, Section 2. The Heart, pp. 61-112. Williams and Wilkins, New York (1979)

Peskin, C.S.: Mathematical aspects of heart physiology. Technical report, Courant Institute of Math. Sciences, New York University, New York, NY, USA (1975).

Horowitz, A., Perl, M., Sideman, S.: Geodesics as a mechanically optimal fiber geometry for the left ventricle, Basic, Res, Cardiol. 88(suppl, 2), 67-74 (1993).

Geerts, L., Bovendeerd, P., Nicolay, K., Arts, T.: Characterization of the normal cardiac rnyofiber field in goat measured with mr-diffusion tensor imaging. Am. J. Physiol.: Heart and Circ. Physiol. 283, H139-H145 (2002).

Beg, M.F., Helm, P.A., McVeigh, E.M., Miller, M.I., Winslow, R.L.: Computational cardiac anatomy using mri. Magn. Reson. Med. 52, 1167-1174 (2004).

Chen, J., Liu, W., Zhang, H., Lacy, L., Yang, X., Song, S.K., Wickline, W.A., Yu, X.: Regional ventricular wall thickening reflects changes in cardiac fiber and sheet structure during contraction: quantification with diffusion tensor mri. Am. J. Physiol.: Heart and Circ. Physiol. 289, H1898-H1907 (2005).

Streeter, D., Bassett, D.: An engineering analysis of myocardial fiber orientation in pig's left ventricle in systole. The Anatomical Record 155(4), 503-511 (2005).

LeGrice, I.J., Smaill, B.H., Chai, L.Z., Edgar, S.G., Gavin, J.B., Hunter, P.J.: Ventricular myocyte arrangement and connective tissue architecture in the dog. Am. J. Physiol.: Heart arid Circ. Physiol. 269 (1995).

Rohmer, D., Sitek, A., Gullberg, G.T.: Reconstruction and visualization of fiber and laminar structure in the normal human heart from ex vivo diffusion tensor magnetic resonance imaging (dtmri) data. Invest. Radiol. 42(11), 777-789 (2007).

Lombaert, H., Peyrat, J.-M., Croisille, P., Rapacchi, S., Fanton, L., Clarysse, P., Delingette, H., Ayache, N. Statistical analysis of the human cardiac fiber architecture from DT-MRI. In: Metaxas, D.N., Axel, L. (eds.) FIMH 2011. LNCS, vol. 6666, pp. 171-179. Springer, Heidelberg (2011).

Ben-Shahar, O., Zucker, S.W.: The perceptual organization of texture flow: A contextual inference approach. IEEE TPAMI 25(4) (2003).

Savadjiev, P., Strijkers, G.J., Bakermans, A.J., Piuze, E., Zucker, S.W., Siddiqi, K.: Heart wall myofibers are arranged in minimal surfaces to optimize organ function. Proc. Natl. Acad. Sci. USA 109(24), 9248-9253 (2012)

Koenderink, J.: Solid shape, vol. 2. Cambridge Univ. Press (1990).

Bayer; J., Blake, R., Plank, G., Trayanova, N.: A novel rule-based algorithm for assigning myocardial fiber orientation to computational heart models. Annals of biomedical engineering (40) 10), 2243-2254 (2012).

P. J. Olver and J. Pohjanpelto, "Maurer—Cartan forms and the structure of lie pseudo-groups," Selecta. Math,, vol. 11, No. 1, pp. 99-126, 2005.

O. Faugeras, Caftan's Moving Frame Method and Its Application to the Geometry and Evolution of Curves in the Euclidean, Affine and Projective Planes. New York, NY, USA: Springer, 1994.

T. Flash and A. A. Handzel, "Affine differential geometry analysis of human arm movements," Biol. Cybern., vol. 96, No. 6, pp. 577-601, 2007.

M. Boutin and P.-L. Bazin, "Structure from motion: A new look from the point of view of invariant theory," Siam J. Appl, Math., vol. 64, No. 4, pp. 1156-1174, 2004.

O. Ben-Shahar and S. W. Zucker, "The perceptual organization of texture flow: A contextual inference approach," IEEE Trans. Pattern Anal. Mach. Intell., vol. 25, No. 4, pp. 401-417, Apr. 2003.

Savadjiev, G. L. Kindlmann, S. Bouix, M. E. Shenton, and C.-F. Westin, "Local white matter geometry from diffusion tensor gradients," NeuroImage, vol. 49, No. 4, pp. 3175-3186, 2010.

E. Calabi, P. J. Olver, C. Shakiban, A. Tannenbaum, and S. Haker, "Differential and numerically invariant signature curves applied to object recognition," Int. J. Comput. Vision, vol. 26, No. 2, pp. 107-135, 1998

P. J. Olver, "Joint invariant signatures," Found. Comput. Math., vol. 1, No. 1, pp. 3-68, 2001.

E. Piuze, J. Sporring, and K. Siddiqi, "Moving frames for heart fiber geometry," Inform. Process. Med. Imaging, vol. 23, pp. 524-535, 2013.

E. Piuze, H. Lombaert, J. Sporring, G. J. Strijkers, A. J. Backermans, and K. Siddiqi, "Atlases of cardiac fiber differential geometry," in Proc. 7th Int. Conf, Functional Imag. Modeling Heart, 2013, pp. 442-449.

P. Savadjiev, G. J. Strijkers, A. J. Bakermans, E. Piuze, S. W. Zucker, and K. Siddiqi, "Heart wall myofibers are arranged in minimal surfaces to optimize organ function," Proc. Nat. Acad. Sci. USA., vol. 109, No. 24, pp. 9248-9253, 2012.

P. Savadjiev, S. W Zucker, and K. Siddiqi, "On the differential geometry of 3d flow patterns: Generalized helicoids and diffusion mri analysis." in Proc. Int. Conf. Comput. Vis., 2007, pp. 1-8.

H. Flanders, Differential Forms with Applications to the Physical Sciences, Mineloa, New York, USA: Dover, 2012.

W Press, S. Teukolsky, W. Vetterling, and B. Flannery, Numerical Recipes: The Art of Scientific Computing, 3rd ed. Cambridge, U.K.: Cambridge Univ. Press, 2007.

M. J. Powell, "The BOBYQA algorithm for bound constrained optimization without derivatives," Cambridge NA Rep. NA2009/06, Univ. Cambridge, Cambridge, U.K., 2009.

T. Needham, Visual Complex Analysis. Oxford, U.K.: Clarendon, 1998.

E. Piuze, P. G. Kry, and K. Siddiqi, "Generalized helicoids for modeling hair geometry," Cornput. Graph. Forum, vol. 30, No. 2, pp. 247-256, 2011.

S. H. Gilbert, A. P. Benson, P. Li, and A. V. Holden, "Regional localisation of left ventricular sheet structure: Integration with current models of cardiac fibre, sheet and band structure," Eur. J. Cardio-Thoracic Surg., vol. 32, No. 2, pp. 231-249, 2007.

Toussaint, N., Sermesant, M., Stoeck, C.T., Kozerke, S., Batchelor, P.G. In vivo human 3D cardiac fibre architecture: reconstruction using curvilinear interpolation of diffusion tensor images. In: MICCAI (2010).

D. F. Scollan, A. Holmes, R, Winslow, and J. Forder, "Histological validation of myocardial microstructure obtained from diffusion tensor magnetic resonance imaging," Am. J. Physiol, Heart Circulatory Physiol., vol, 275, No. 6, pp. H2308-H2318, 1998.

L. Geerts, P. Bovendeerd, K. Nicolay, and T. Arts, "Characterization of the normal cardiac myofiber field in goat measured with mr-diffusion tensor imaging," Am, J. Physioi., Heart Circ. Physiol., vol. 283, pp. H139-145, 2002.

H. Lornbaert, J. Peyrat, P. Croisille, S. Rapacchi, L. Fanton, F. Cheriet, P. Clarysse, I.Magnin, H. Delingette, and N. Ayache, "Human atlas of the cardiac fiber architecture: Study on a healthy population," IEEE Trans.Med. Imag., vol. 31, No. 7, pp. 1436-1447, Jul. 2012.

J. C. Walker, J. M. Guccione, Y. Jiang, P. Zhang, A.W. Wallace, E. W. Hsu, and M. B. Ratcliffe, "Helical myofiber orientation after myocardial infarction and left ventricular surgical restoration in sheep," J. Thoracic Cardiovascular Sung., vol. 129, No. 2, pp. 382-390, 2005.

J. Chen, W. Liu, H. Zhang, L. Lacy, X. Yang, S.-K. Song, W. A. Wickline, and X. Yu, "Regional ventricular wall thickening reflects changes in cardiac fiber and sheet structure during contraction: Quantification with diffusion tensor MRI," Am. J. Physiol., Heart Circ. Physiol., vol. 289, pp. H1898-1907, 2005.

D. Streeter and D. Bassett, "An engineering analysis of myocardial fiber orientation in pig's left ventricle in systole," Anatomical Rec., vol. 155, No. 4, pp, 503-511, 2005.

R. Deriche and D. Tschumperlé, "Diffusion PDE's on vectorvalued images: Local approach and geometric viewpoint," IEEE Signal Process. Mag., vol. 19, No. 5, pp. 16-25, 2002.

(56) References Cited

OTHER PUBLICATIONS

M. Martin-Fernandez, E. M. noz Moreno, L. Cammoun, J.-P. Thiran, C.-F. Westin, and C. Alberola-López, "Sequential anisotropic multichannel wiener fiitering with Rician bias correction applied to 3d regularization of DWI data," Med. Image Anal., vol. 13, pp. 19-35, 2009.

Streeter DD, Powers WD, Alison Ross M, Torrent-Guasp F (1978) Three-dimensional fiber orientation in the mammalian heart, Cardiovascular System Dynamics (MIT Press, Cambridge, MA), pp. 73-84.

Streeter DD, Spotnitz HM, Patel DP, Ross J, Sonnenblick EH (1969) Fiber orientation in the canine left ventricle during diastole and systole. Circ Res 24:339-347.

Streeter DD, Hanna Wt (1973) Engineering mechanics for successive states in canine left ventricle myocardium. II. Fiber angle and sarcomere length. Circ Res 33:656-664.

Peskin CS (1975) Mathematical Aspects of Heart Physiology (New York University, New York).

Peskin CS (1989) Fiber architecture of the left ventricular wall: An asymptotic analysis. Commun Pur Appl Math 42:79-113.

Neville AC (1993) Biology of Fibrous Composites: Development Beyond the Cell Membrane (Cambridge Univ Press, Cambridge, UK).

Gilbert S, Benson A, Li P, Holden A (2007) Regional localisation of left ventricular sheet structure: Integration with current models of cardiac fibre, sheet and band structure. Eur J Cardiothorac Surg 32:231-249.

Blair DE, Vanstone JR (1978) A generalization of the helicoid. Minimal Submanifolds and Geodesics (Kaigai Publ, Tokyo), pp. 13-16.

Barbosa JM, Dajczer M, Jorge LP (1984) Minimal ruled submanifolds in spaces of constant curvature. Indiana U Math J 33:531-547.

\* cited by examiner

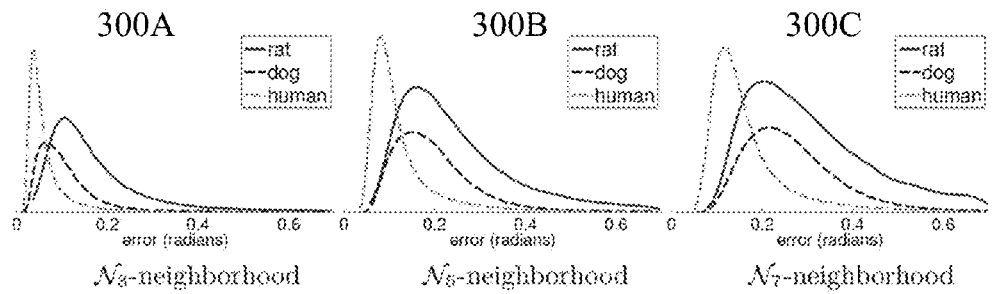
Figure 3
Figure 4
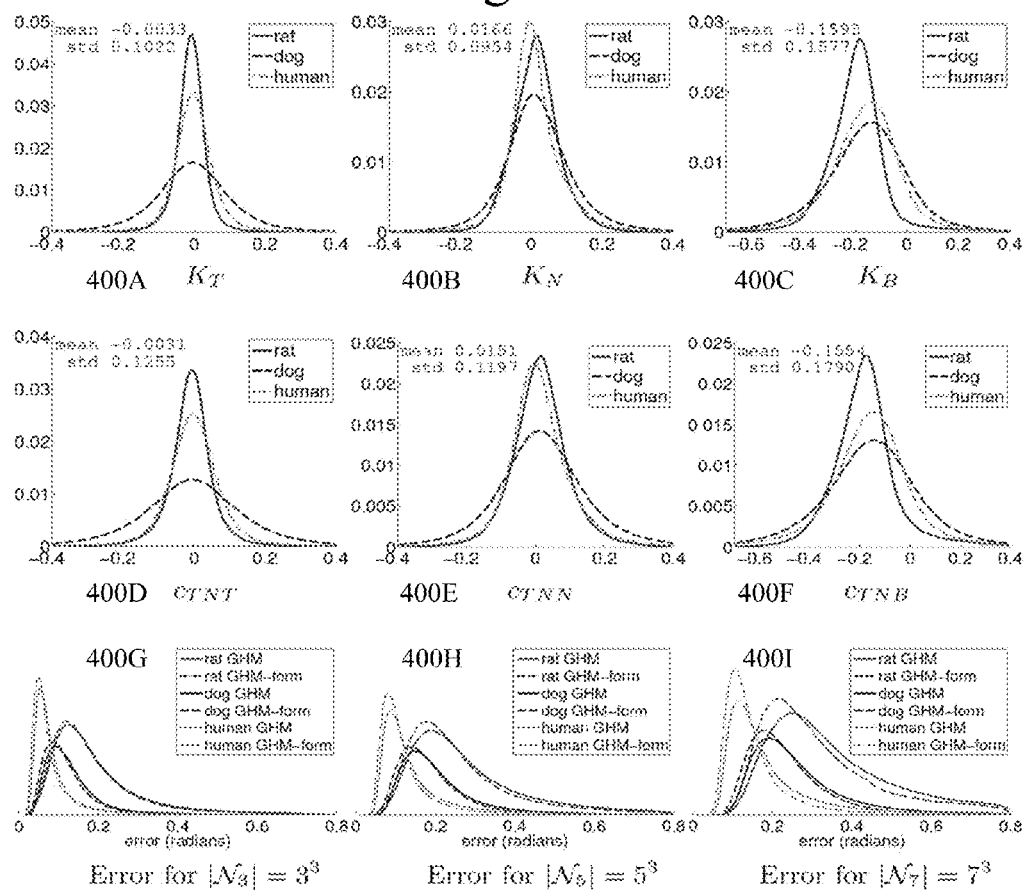

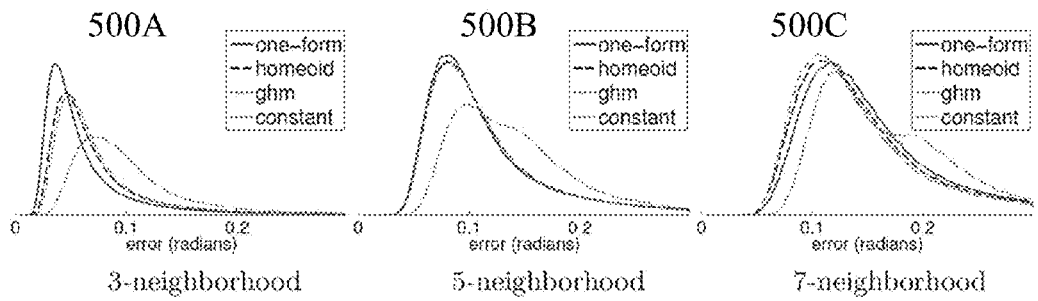
Figure 5
Figure 6
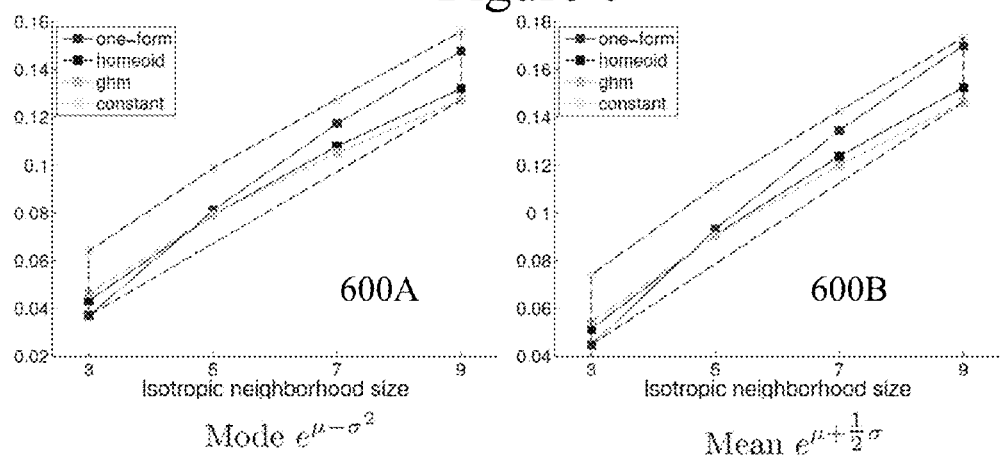
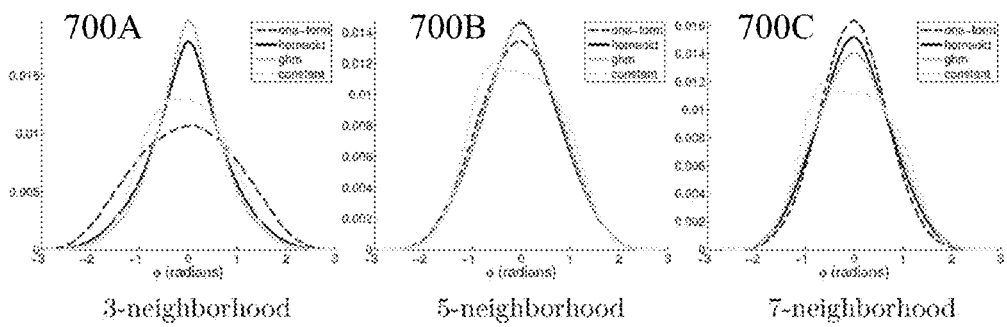
Figure 7

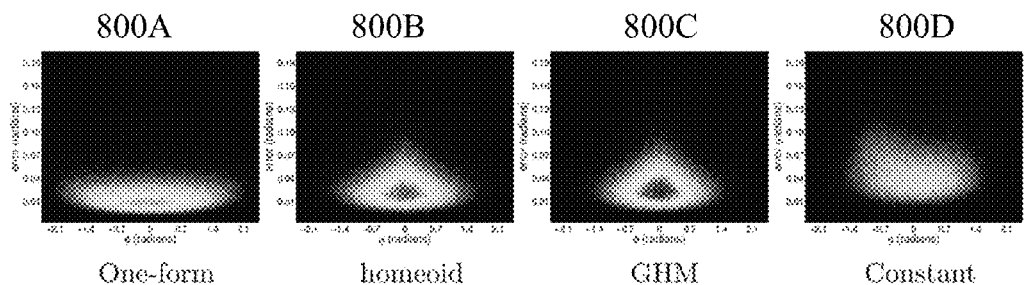
Figure 8
Figure 9
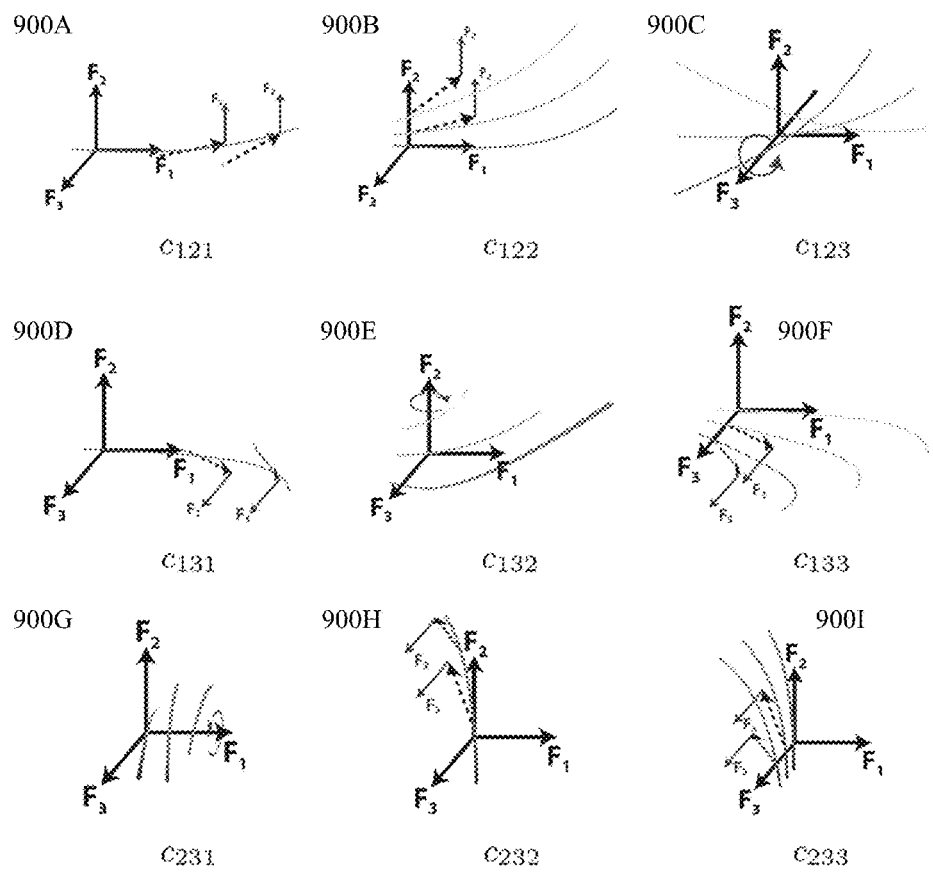

Helical rotation
1700A

Wall curvature
1700B

Wall curvature
1700C 2500A  2500B  2500C $\epsilon_1$ (rads)   $\epsilon_2$ (rads)   $\epsilon_3$ (rads)
2600A        2600B        2600C

METHODS OF MODELLING AND CHARACTERISING HEART FIBER GEOMETRY

CROSS-REFERENCE TO RELATED APPLICATIONS

This patent application claims the benefit of U.S. Provisional Patent Application 61/993,600 filed May 15, 2014, the entire contents of which are included by reference.

FIELD OF THE INVENTION

This invention relates to heart fiber geometry and more particularly to improved methods of optimizing connection forms in local neighbourhoods and employing these to statistically analyse heart fiber geometry using diffuse magnetic resonance imaging data.

BACKGROUND OF THE INVENTION

Cardiac myofibers are densely packed in the heart wall and are locally aligned to helical curves. Helices act as geodesics between points in the myocardium and mathematical analyses support the view that this alignment is mechanically optimal. As a result, geometric descriptions of cardiac fibers using the helix angle, taken to be the projected angle between the fiber direction and the short-axis plane (see first image 100A in FIG. 1), are popular within the prior art. Several accounts from both small-scale histology and voxel-scale studies based on Diffusion MRI (dMRI) report that along a transmural penetration line from the heart's outer to inner wall, the helix angle varies smoothly and regularly undergoing a total change in orientation of about 120°. The range of the transverse angle, which is the angle formed by a fiber moving away from a plane perpendicular to the transmural direction, is much smaller, about ±10°, and is therefore often ignored in the literature, The analysis of myofibers from histological slices is cumbersome and their invasiveness does not easily admit an association with the original intact three-dimensional geometry. Thus, many modern analysis methods work with cardiac fiber orientation data derived from dMRI measurements. However, the scale at which current dMRI measurements are made is at least one order of magnitude larger than the length of individual cardiomyocytes The measured signal therefore reflects the composite behaviour of large groups of cardiac muscle cells within the collagen matrix (see third image 100C in FIG. 1). Within the prior art a promising characterization of the collective geometrical variation of cardiac fibers, using a method derived from texture flow analysis, has been reported. This work concluded that that the cardiac fiber directions across three mammalian species, the rat, the canine and the human, are locally described by a particular minimal surface, the generalized helicoid model (GHM).

However, a limitation of the GHM is that its streamlines lie on a planar manifold in spite that the heart wall is curved (see first image 100A in FIG. 1). The GHM thus captures the variability of cardiac fibers in a plane tangent to the local cardiac wall but not orthogonally to it. Moreover, experimental results have shown that the GHM is only accurate in the immediate neighborhood of a voxel, with fitting errors growing rapidly as the neighborhood in which the fits are applied is increased.

Accordingly it would be beneficial to provide an alternate model for modeling cardiac fibers within heart walls that removes the limitations of GHM.

SUMMARY OF THE INVENTION

It is an object of the present invention to heart fiber geometry and more particularly to improved methods of optimizing connection forms in local neighbourhoods and employing these to statistically analyse heart fiber geometry using diffuse magnetic resonance imaging data.

The inventors have attached a local frame field to the fiber and transmural directions and study the full differential geometry of this moving frame through the Maurer-Cartan connection one-forms. Further, the inventors demonstrate that form-based models on which the streamlines lie on ellipsoidal shells or homeoids give lower fitting errors than the generalized helicoid model fits.

More precisely within the method of moving frames, the Maurer-Cartan form is an operator that measures the differential structure of a manifold which is typically applied in a forward manner to study the geometrical characteristics of the manifold under consideration. However, the inventors have applied the theory of moving frames in the reverse direction such that the Maurer-Cartan connection forms are manipulated to generate manifolds or embeddings based on certain assumptions of their differential structure. Beneficially, this approach allows characterization of a smooth frame field in three dimensions as a parameterization on the space of Maurer-Cartan connection forms. By introducing various connection form embeddings for studying frame fields, the inventors show that GHM can fully describe locally using a combination of connection forms. Further, the inventors introduce a fitting energy for estimating connection forms from arbitrary smooth frame fields. Based upon applying these frame fields to dMRI data and studying its differential geometry, not only can the inventive methods described corroborate biological measurements of heart fiber orientation but they also provide novel biological views in respect of heart fiber orientation.

In accordance with an embodiment of the invention there is provided a method
acquiring data relating to a heart;
establishing a model relating to the heart;
establishing a fitting energy associated with the model;
iterating the model in dependence upon a mathematical process and the acquired data;
calculating a new fitting energy associated with the iterated model; and
determining whether the new fitting energy meets a predetermined threshold, wherein
when the predetermined threshold is met the iterative process is terminated; and
when the predetermined threshold is not met the iterative process continues.

In accordance with an embodiment of the invention there are provided computer executable instructions stored in a non-volatile, non-transient computer memory, the computer executable instructions for execution by a microprocessor and relating to a process comprising the steps of:
acquiring data relating to a heart;
establishing a model relating to the heart;
establishing a fitting energy associated with the model;
iterating the model in dependence upon a mathematical process and the acquired data;
calculating a new fitting energy associated with the iterated model; and determining whether the new fitting energy meets a predetermined threshold, wherein
when the predetermined threshold is met the iterative process is terminated; and
when the predetermined threshold is not met the iterative process continues.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 3 depicts the one-form extrapolation error for neighborhoods of size $|N_i|=3^3$, $5^3$, $7^3$;

FIG. 4 depicts the one-form approximation to the GHM for the neighborhood $N_3$ together with the error of each model a function of $N_i$;

FIG. 5 depicts error of fit for the different models analyzed for the human heart where the results are shown for isotropic voxel neighbourhoods of size $3^3$, $5^3$, $7^3$;

FIG. 6 depicts log-normal fits of the human heart extrapolation error;

FIG. 7 depicts the rotational angle $\phi$ of the different models analyzed for the human heart in isotropic voxel neighbourhoods of size $3^3$, $5^3$, $7^3$;

FIG. 8 depicts joint histograms of the angular errors e and $\phi$ for the human heart for different models for isotropic $3^3$ neighborhoods;

FIG. 9 depicts the geometry characterized by connection forms;

DETAILED DESCRIPTION

Figure 1:
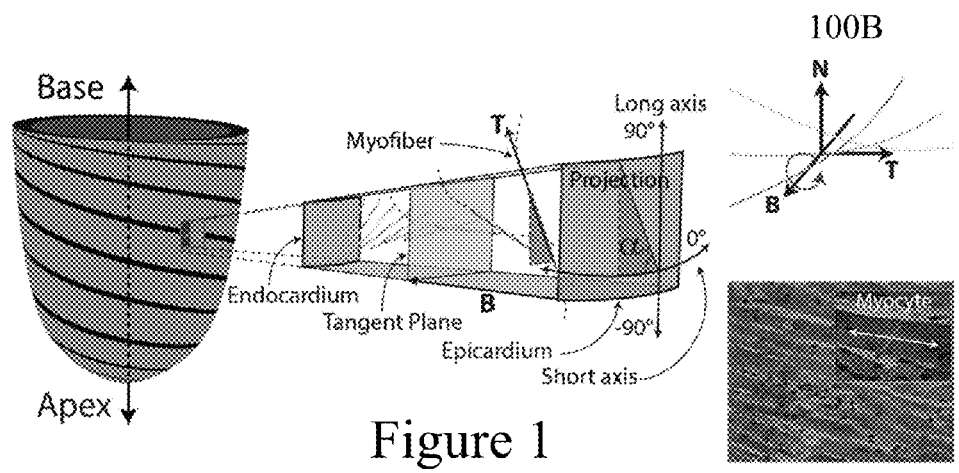
FIG. 1 depicts the definition of the helix angle, the transmural change in the helix angle in directions orthogonal to the heart wall tangent plane and a histological slice of cardiac tissue showing individual elongated cardiomyocytes and their nuclei (dark) in the intercellular collagen network.

The present invention is directed to heart fiber geometry and more particularly to improved methods of optimizing connection forms in local neighbourhoods and employing these to statistically analyse heart fiber geometry using diffuse magnetic resonance imaging data.

The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment. It being understood that various changes may be made in the function and arrangement of elements without departing from the spirit and scope as set forth in the appended claims.

A1. The Maurer-Cartan Form

The inventors characterize the differential geometry of fibers in the heart wall by measuring the manner in which they turn locally. Accordingly, a frame field is constructed $F_1, F_2, F_3 \in \Re^3$, $F_i \cdot F_j = \delta_{ij}$, where $\delta_{ij}$ is the Kronecker delta, in such a manner that the turning of the frame field characterizes the turning of the heart wall fibers. The frame field is then expressed as a rotation of the Cartesian frame $[e_1 e_2 e_3]$ in Equation (1) where the attitude matrix $A \in SO(3)$ is a smoothly varying orthonormal matrix, and where the basis vectors $e_j$ are treated as symbols such that $F_i = a_{ij} e_j$. As a result the differential geometry of the fibers is new directly characterized by the attitude transformation. Its differential structure is given by Equation (2) where d is the differential operator, $A^{-1}=A^T$, $C=(dA)A^{-1}$ is the Maurer-Cartan form, and where for simplicity the notation $dF_i=\Sigma_j c_{ij} F_j$ is used.

$$[F_1 F_2 F_3]^T = A[e_1, e_2, e_3]^T \quad (1)$$

$$d\begin{bmatrix} F_1 \\ F_2 \\ F_3 \end{bmatrix} = \begin{bmatrix} dF_1 \\ dF_2 \\ dF_3 \end{bmatrix} = (dA)\begin{bmatrix} e_x \\ e_y \\ e_z \end{bmatrix} = (dA)A^{-1}\begin{bmatrix} F_1 \\ F_2 \\ F_3 \end{bmatrix} = C\begin{bmatrix} F_1 \\ F_2 \\ F_3 \end{bmatrix} \quad (2)$$

The Maurer-Cartan matrix is skew symmetric, i.e. $C=-C^T$. Hence it has at most 3 independent, non-zero elements: $c_{12}$, $c_{13}$, and $c_{23}$. Each $c_{ij}$ is a one-form in $\Re^3$ that can be contracted on a vector $v=[v_1, v_2, v_3]^T \in \Re^3$ to yield the initial rate of turn of $F_i$ towards $F_j$ when moving in the direction of v. The inventors denote this contraction $c_{ij}(v)$, which is found to be $c_{ij}(v)=\nabla_v F_i \cdot F_j|_x$, where $x \in \Re^3$ is a point in the fiber field and $\nabla_v F_i$ is the covariant derivative of $F_i$ in the direction v. Accordingly, $c_{ij}(v)$ is defined by Equation (3) where the components of the frame vectors are enumerated as $F_i=[F_{i1}, F_{i2}, F_{i3}]^T$ where $\delta_x=\delta/\delta x$ is used to denote partial derivatives. Since we are interested in studying the change of the frame field in the direction of its basis vectors we study the contractions $c_{ijk} \equiv c_{ij}\langle F_k \rangle$. It should be noted that the frame field $F_1$, $F_2$, $F_3$ has 3 degrees of freedom. Since this field roams a 3-dimensional space, a linear model of the spatial change of the frame field must have 9 degrees of freedom, which are embodied in $e_{ijk}$.

$$c_{ij}\langle v \rangle = [F_{j1} F_{j2} F_{j3}] \begin{bmatrix} \delta_x F_{i1} \delta_y F_{i1} \delta_z F_{i1} \\ \delta_x F_{i2} \delta_y F_{i2} \delta_z F_{i2} \\ \delta_x F_{i3} \delta_y F_{i3} \delta_z F_{i3} \end{bmatrix} \begin{bmatrix} v_1 \\ v_2 \\ v_3 \end{bmatrix} \quad (3)$$

The abstraction and the comprehensiveness in the one-form description of the geometrical behavior of a frame field can be harnessed to develop models that are descriptive of the variability of cardiac fiber orientations across multiple species. Accordingly, in section 3 the inventors introduces a class of fiber models based on one-forms and re-introduce the GHM as a planar approximation to the complete one—form parameterization.

A2. Measures on a Discrete Fiber Frame Field

The inventors analyze hearts represented as diffusion MRI volumes embedded in 3D rectangular lattices with coordinates $x=xe_1+ye_2+ze_3=[x, y, z]^T \in Z^3$. A tangent vector T is identified as the principal eigenvector of the diffusion tensor field. Consistency in T amongst voxel neighbours is enforced by adopting an adaptive cylindrical coordinate system. The centroid $c_z$ of the chamber within each short-axis slice, s, is first determined. T(m) is then made to turn clockwise with respect to that centroid through Equation (4) where $l(s_z)$ is the local approximation of the heart's long-axis.

$$T(x) \rightarrow \text{sign}((T \times (x-c_z)) \cdot l(s_z))T(x) \quad (4)$$

For all the hearts that we consider, $l(s_z)$ approximately coincides with the world's z axis. In accordance with the spirit of the GHM method the heart transmural direction B is estimated as the gradient vector of a distance transform produced as follows the binary image (mask) of the heart is closed using mathematical morphological operations;

the closest distance to the heart wall is evaluated at every point;

the gradient of the distance transform is computed, and the skeletal points of colliding fronts are removed and interpolated by thresholding the magnitude of the gradient vectors.

The normals $\hat{B}$ are then aligned to point from outer to inner wall. With T and $\hat{B}$ we specify a local frame as given by Equations (5A) to (5C) where B is the part of $\hat{B}$ orthogonal to T. From here on, the inventors use the symbols T, N, and B interchangeably with the corresponding symbols $F_j$. Further, the inventors also refer to the local plane spanned by T and N as the tangent plane.

$$F_1 = \frac{T}{\|T\|} \quad (5A)$$

$$F_2 = N = F_3 \times F_1 \quad (5B)$$

$$F_3 = B = \frac{(\hat{B} - (\hat{B} \cdot T)T)}{\|\hat{B} - (\hat{B} \cdot T)T\|} \quad (5C)$$

A2.1 One-Form Intuition

Figure 2:
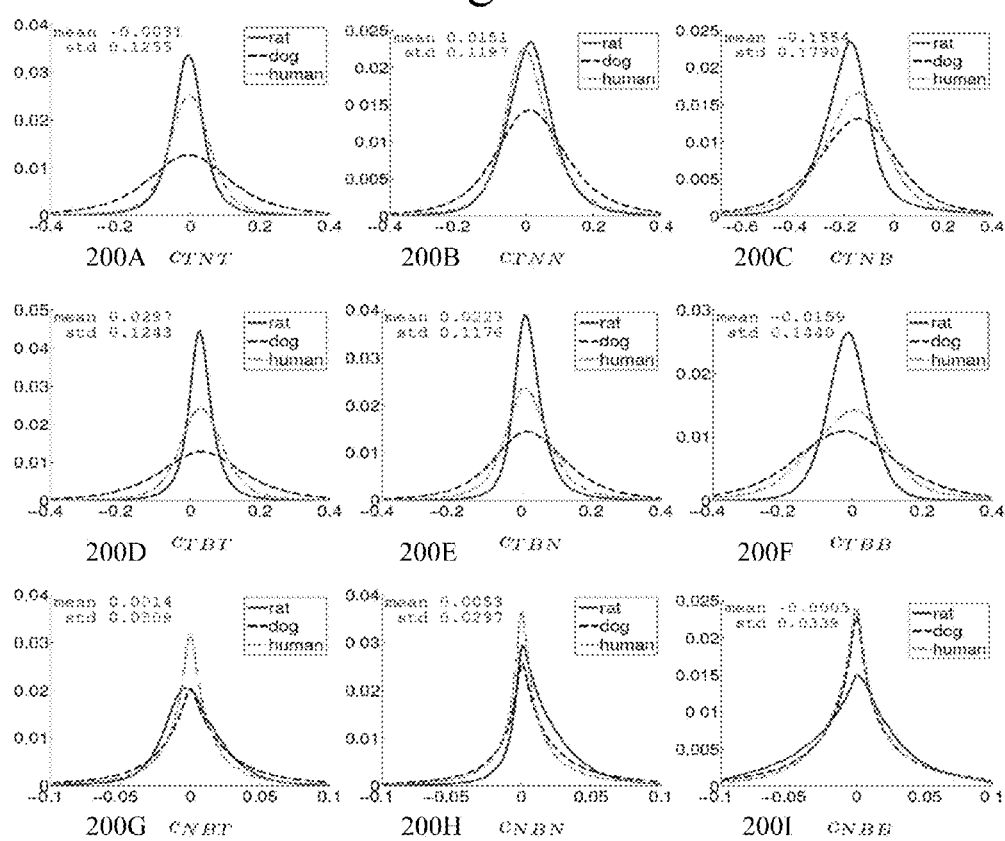
FIG. 2 depicts histogram of $c_{ijk} \equiv c_{ij} \langle F_k \rangle$ for rat, human, and with measures normalized such that the horizontal axis is in millimeters.

One-form contractions $c_{ijk}$ can be interpreted as the amount of turning of $F_i$ towards $F_j$, in the direction $F_k$. For example, $c_{TNB}$ describes a transmural rotation of T towards N, as shown in second image 100B in FIG. 1. $c_{ijk}$ were computed at each voxel from the discrete fiber frame field combined with Equation (3). The resulting histograms for three species (rat, canine, human) are shown in FIG. 2 and illustrate statistics on the local turning of the frame field. The rotations of T towards N, $c_{TNB}\langle F_k \rangle$, are intuitively linked to the curvature parameters of the GHM method in the prior art. These rotations intuitively describe the manner in which fibers turn in the tangent plane of the heart, $c_{TNT}$ in first image 200A in FIG. 2, describes their tangential curvature, $c_{TNN}$ in first image 200B in FIG. 2, their fanning in the tangent plane, and $c_{TNN}$ in second image 100B in FIG. 1, their transmural turning or equivalently the rate of change of the helix angle. This is arguably the most salient variation of the cardiac fibers. The rotations of T towards B, $c_{TB}\langle F_k \rangle$, expresses the turning of the fibers towards the inner wall, $c_{TBT}$ effectively measures the first local curvature of the heart, $c_{TBN}$ describes a twisting of the tangent plane and the rate of change of the transverse angle, and $c_{TBB}$ measures a fanning or thickening of the local fiber population away from the tangent plane, towards the inner wall. As shown in seventh to ninth images 200G to 200I in FIG. 2 the remaining rotations of N towards B, $c_{NB}\langle F_k \rangle$ are an order of magnitude smaller in all three directions which indicates that the frame field axis N is constrained within the local tangent plane. $c_{NBT}$ measures a twisting of the tangent plane, $c_{NBN}$ the second curvature of the heart wall and $c_{NBB}$ a transmural fanning or thickening.

A2.2 The One-Form Model

The Maurer-Cartan form extrapolates the local shape to first order as given by Equations (6) and (7) where h is an offset from the point at which the frame is expressed and $\hat{T}_h$ represents the predicted direction of this neighbor by the one-form extrapolation to first-order approximation. As within the GHM method the inventors construct an error measure by computing the average angular difference between the measured and predicted directions in an isotropic neighborhood N as given by Equation (8) where $|N_i|=i^3$ for odd $i \in Z$ and $T_h$ is the true neighbours measured direction.

$$\tilde{T}_h = T + c_{TN}\langle h\rangle N + c_{TB}\langle h\rangle B \quad (6)$$
$$= T + (c_{TNT}h\cdot T + c_{TNN}h\cdot N + c_{TNB}h\cdot B)N +$$
$$(c_{TBT}h\cdot T + c_{TBN}h\cdot N + c_{TBB}h\cdot B)B \quad (7)$$

$$e(N_i) = \frac{1}{|N_i|}\sum_{h\in N_i}\arccos\left(T_h\cdot\frac{\tilde{T}_h}{\|\tilde{T}_h\|}\right) \quad (8)$$

The associated errors of fit for different species are shown in FIG. 3. Diffusion MRI noise and resolution, heart size, and underlying fiber geometry are factors that account for the error disparity across different species. We delay further analysis of these errors until Section 3, where they will be compared against those of the other models the inventors introduce next.

A2.3 The Generalized Helicoid as a Subset of the One-Form Model

The generalized helicoid model of the GHM within the prior art expresses the local fiber direction in a plane tangent to the heart wall. Within the local coordinate frame, the fiber direction at a point $x = x_T T + x_N N + x_B B \in \Re^3$ is given as the angle defined in Equation (9) where $K_* \in R$ are the GHM curvature parameters.

$$\theta(x, K_T, K_N, K_B) = \arctan\left(\frac{K_T x_T + K_N x_N}{1 + K_N x_T - K_T x_N}\right) + K_B x_B \quad (9)$$

Direct calculations show that a frame field spanned by $T(\theta)$, $N(\theta)$, $B(\theta)$ has instantaneous turning given by $c_{TN}\langle T(\theta)\rangle = K_T$, $c_{TN}\langle N(\theta)\rangle = K_N$, and $c_{TN}\langle B(\theta)\rangle = K_B$ with the remaining one-forms all being zero. The GHM parameters can thus be estimated directly using Equation (3) and the GHM model may be evaluated directly using Equation (7) and central differences as an alternative to the generative model. To compare these two representations, the parameter vector $K = (K_T, K_N, K_B)$ of the GHM was estimated at each voxel using a standard Nelder-Mead optimization scheme. The problem was formulated as the selection of the parameters K which minimize an extension of Equation (8) where $\tilde{T}_h \to \tilde{T}_h(K) = (\cos\theta, \sin\theta, 0)$ and $\theta = \theta(K)$ as given by Equation (9).

The results for the fitting error and a comparison with the one-forms are shown in FIG. 4. These results indicate that the one-form model is able to capture the GHM's parameterization accurately and that it consistently yields lower errors. Note that in addition to an improved fitting method which is continuous rather than discrete the inventive method estimates heart wall normals slightly differently than is done within the GHM prior art. Consequently, the inventors parameter estimates are more precise and still support the overall shape distribution reported within the prior art. Accordingly, within the subsequent description the inventors when considering the GHM methodology will be referring to and using its one-form approximation, which they refer to as the ghm-form.

Accordingly, the inventors then proceeded to introduce a differential model, the homeoid, that can also be expressed using a subset of the one-forms, and has the advantage that it is intuitively connected to the large-scale structure of the heart by enforcing the ellipsoidal topology of the local tangent plane.

A2.4 The Generalized Helicoid on an Ellipsoid is a Homeoid

The calculations within Section 2.3 can be applied to model fibers with smoothly varying fiber orientations, such that the differential operations are well defined. Motivated by evidence that fibers wind around the heart wall while remaining approximately parallel to the tangent plane to the wall at each location the inventors consider a specialization to the case where the fibers lie locally on thin homeoids, which are shells composed of two concentric and similar ellipsoids.

As introduced in Section 1, the Maurer-Cartan form has only 3 independent one-forms: $c_{TN}\langle\bullet\rangle$, $c_{TB}\langle\bullet\rangle$ and $c_{NB}\langle\bullet\rangle$ each with 3 associated spatial degrees of freedom, for a total of 9 possible combinations. Working with the intuition given in Section 2.2 of each $c_{ijk}$, this is a convenient space to develop models of fiber geometry. For example, in Section 2.3 the inventors showed that for the GHM only $c_{TN}\langle T\rangle$, $c_{TB}\langle T\rangle$ and $c_{NB}\langle T\rangle$ are non-zero. Based on a general description of the cardiac fiber architecture as collections of fibers that (i) vary smoothly and (ii) are locally constrained to the tangent space of smooth and orthogonal surfaces to the heart wall, the following one-form contractions given in Equation (10) must occur.

$$c_{TN}\langle T\rangle = \alpha; c_{TN}\langle N\rangle = \beta; c_{TN}\langle B\rangle = \gamma; c_{TB}\langle B\rangle \approx 0; c_{NB}\langle B\rangle \approx 0 \quad (10)$$

Locally, these fibers lie in the tangent plane of a thin homeoid. The parameter fields $\alpha$, $\beta$ and $\gamma$ are introduced as the curvature parameters of the fibers. $c_{NBB}$ must be zero otherwise the fibers could move in and out of the local tangent plane and the hypothesis (ii) would not be satisfied. The remaining contractions specify the shape of the homeoid and accordingly are given by Equation (11) where $\rho_1$ and $\rho_2$ are the radii fields of the oscillating ellipsoid. Using Equation (7), the model can be employed to extrapolate the orientation of fibers in the neighborhood of a point x. Constraints given by Equations (10) and (11) are satisfied by enforcing the nullity of $c_{TBN}$ and $c_{TBB}$ such that we obtain Equation (12).

$$c_{TN}\langle T\rangle = \frac{1}{\rho_1}; c_{TN}\langle N\rangle = \frac{1}{\rho_2}; c_{TB}\langle N\rangle = 0; c_{NB}\langle T\rangle = 0 \quad (11)$$

$$\tilde{T}_h = T + c_{TN}\langle h\rangle N + (c_{TBT}h\cdot T)B \quad (12)$$

A3. Model Space Comparison

The analytical models of fiber geometry described so far vary in their parametric complexity. The one-form, homeoid and generalized helicoid models respectively have 9, 5, and 3 parameters. We introduce the constant model which will serve as a base-line to which the remaining models can be compared. This parameter-free model simply assumes $\tilde{T}_h = T$ in Equation (7). To compare the different models in terms of their fitting accuracy, we have evaluated each $c_{ijk}$ on the human data set using first-order central differences on $3^3$ neighbors. We then used these one-forms to extrapolate each model using Equations (7) and (8) in isotropic neighbourhoods where $N_i$, where $|N_i| = i^3$ for $i = 3, 5, 7, 9$. FIG. 5 shows a distribution of the error of fit in the human dataset for the different models across increasingly large voxel neighborhoods. Error generally increases with neighborhood size but the relative performance of each model is difficult to assess. Accordingly the inventors therefore fitted a log-normal distribution to each error plot and show the resulting log-normal mode $e^{\mu-\sigma^2}$ and mean $e^{\mu+\frac{1}{2}\sigma^2}$ as a function of neighborhood size in FIG. 6. As expected, the constant model provides an upper bound on the error of fit and is a measure of the smoothness in the data. The one-form model has the lowest error of fit when the neighborhood size reflects the scale at which central differences were computed but behaves poorly for larger neighborhood sizes, which we attribute to local over-fitting. On the other hand, the ghm-form and the homeoid models are well-behaved for all neighborhood sizes and differ only slightly from one another.

In Section 2.4 the inventors showed that their extrapolated $\tilde{T}_h$ axis only differs by the $c_{TBT}$ one-form which is a measure of the curvature of the heart wall. For the human, this value is small and therefore the two models should be very similar. The rat hearts is smaller in size and therefore has larger per voxel curvature. In this case Table 1 shows that the homeoid is a better fit.

TABLE 1

Extrapolation Errors in Radians for Each Species, Differential Model and Neighbourhood $N_i$ from the mode $e^{\mu-\sigma^2}$ and the mean $e^{\mu+\frac{1}{2}\sigma^2}$ of log-normal fits.

| $|N_i|$ | | Rat (mode, mean) | Dog (mode, mean) | Human (mode, mean) |
|---|---|---|---|---|
| $3^3$ | one-form | 0.093, 0.113 | 0.076, 0.092 | 0.039, 0.054 |
| | homeoid | 0.094, 0.115 | 0.085, 0.102 | 0.046, 0.063 |
| | ghm-form | 0.099, 0.118 | 0.089, 0.106 | 0.050, 0.066 |
| | Constant | 0.163, 0.181 | 0.110, 0.128 | 0.070, 0.090 |
| $5^3$ | one-form | 0.146, 0.175 | 0.157, 0.181 | 0.085, 0.112 |
| | homeoid | 0.145, 0.173 | 0.152, 0.176 | 0.085, 0.112 |
| | ghm-form | 0.150, 0.175 | 0.147, 0.171 | 0.085, 0.111 |
| | Constant | 0.271, 0.286 | 0.156, 0.178 | 0.109, 0.135 |
| $7^3$ | one-form | 0.202, 0.239 | 0.220, 0.251 | 0.124, 0.161 |
| | homeoid | 0.200, 0.234 | 0.202, 0.235 | 0.117, 0.152 |
| | ghm-form | 0.206, 0.237 | 0.189, 0.221 | 0.114, 0.147 |
| | Constant | 0.389, 0.402 | 0.189, 0.215 | 0.141, 0.172 |

A moving frame in $\Re^3$ has 3 degrees of freedom of which 2 are captured by the error vector $T-\tilde{T}_h$: the angular difference $e(N)$ between dMR1 orientations and extrapolations specified by Equation (8), and a rotation $\phi$ about T. The third DOF is the rotation $\psi$ of N about T. $\psi$ strongly depends on the calculations of B and much less on the direct measurements. In contrast to the GHM, the homeoid model considers this angle. However, since we focus on the direct measurement of the fiber geometry given by T, then further investigation of $\psi$ is left outside of this description. $\phi$ can be obtained by projecting $T-\tilde{T}_h$, onto the local NB plane and measuring its angle with respect to the frame axis N:

$$\phi = \arctan\frac{(T-\tilde{T}_h)\cdot B}{(T-\tilde{T}_h)\cdot N}, \text{ i.e.}$$

$\phi=(0, \pi)$ and $$\left(\frac{\pi}{2}, \frac{3\pi}{2}\right)$$

respectively indicate alignment with the frame vectors N and B respectively. FIG. 5 showed the marginal distributions of e(x,N) for various neighborhoods sizes and FIG. 7 shows the marginal distributions of $\phi$. In FIG. 8 the inventors show the joint histogram of these marginal distributions for the human heart and for the 4 different models in a $3^3$ extrapolation neighborhood. It is evident that the error along $\phi$ is negligible when e is small. The spread of $\phi$ measures the rotation of the local NB plane, which for the one-form model results in over-fitting for larger neighborhood sizes. Accordingly, the inventors have established a one-form model yielding the lowest fitting error for small neighborhoods and that the homeoid model is as accurate as or better than the GHM depending on the per-voxel curvature of the heart wall.

B1. Structure of the Frame Fields

Let a point $x=\Sigma_i x_i e_i \in \Re^3$ be expressed in terms of the natural orthonormal coordinate system $e_1$, $e_2$, $e_3$. A differential orthonormal frame field embedded in $\Re^3$ is denoted as $F=[f_1, f_2, f_3]^T$: $\Re^3 \to \Re^3$ and defined by $f_i \cdot f_j = \delta_{ij}$, where $\delta_{ij}$ is the Kronecker delta and where $\cdot$ is the inner product, and $f_1 \times f_2 = f_3$, where x is the 3-dimensional cross product. Since the frame $E=[e_1, e_2, e_3]^T$ forms an orthonormal basis for $\Re^3$, F can be expressed as the rotation $f_i = \Sigma_j a_{ij} e_j$, where the elements of the attitude matrix A $A=\{a_{ij}\} \in \Re^{3\times 3}$ are differentiable, and $A^{-1}=A^T$. Treating $f_i$ and $e_j$ as symbols then this rotation can be written in matrix form as given by Equation (13).

$$[f_1, f_2, f_3]^T = A[e_1, e_2, e_3]^T \Leftrightarrow F = AE \quad (13)$$

$$dF = (dA)E + A(\overrightarrow{dE}^0) = (dA)A^{-1}F = CF \quad (14)$$

$$df_i = \sum_j c_{ij} f_j \quad (15)$$

Since each $e_i$ is constant, the differential geometry of the frame field is completely characterized by the attitude matrix A. Now taking the exterior derivative on both sides of Equation (13) we arrive at Equation (14) wherein d denotes the exterior derivative operator, and $C=(dA)A^{-1}=\{c_{ij}\} \in \Re^{3\times 3}$ is the Maurer-Cartan matrix of one-forms $c_{ij}$. Now writing $f_i$ as symbols then Equation (14) can be understood as Equation (15).

The Maurer-Cartan matrix is skew symmetric and accordingly Equation (16) applies such that there are at most 3 independent, non-zero elements: $c_{12}$, $c_{13}$ and $c_{23}$. The differential of the elements $a_{ij}(x): \Re^3 \to \Re$ of A is expressed in terms of $dx^k$, the natural basis for one-forms in $R^3$, and is given by Equation (17).

$$C = \begin{bmatrix} 0 & c_{12} & c_{13} \\ -c_{12} & 0 & c_{23} \\ -c_{13} & -c_{23} & 0 \end{bmatrix} \quad (16)$$

$$da_{ij} = \sum_k \frac{\delta a_{ij}}{\delta x_k} dx^k \quad (17)$$

One-forms as noted supra are differential operators that may be applied to tangent vectors through a process denoted contraction, written as $dw(v) \in \Re$ for a general one-form dw on $\Re^3$ and tangent vector $v \in \Re^3$. The contraction of $dw=\Sigma_k w_k dx^k$ on v is written as a bilinear operation on the canonical projection of v: $dw(v)=\Sigma_i w_i de_i(\Sigma_j v_j e_j)=\Sigma_i w_i v_i$. Hence, when contracted, the elements of C in Equation (14)

are given by Equation (18) and they express the amount of turning of $f_j(x)$ when x moves in the direction v. This analysis naturally applies to frame fields embedded in $\Re^2$ by setting $f_3$ to be constant. In that case, C is a 2×2 matrix with a single one-form $c_{12}$ which describes the in-plane turning of the frame; hence, if $f_1$ is the tangent of a planar curve and $f_2$ its normal, then $c_{12}(f_1)$ is the curves curvature and $c_{12}(f_2)$ its fanning.

$$c_{ij}\langle v\rangle = \sum_k a_{jk} \sum_l \frac{\delta a_{ik}}{\delta x_l} v_l \tag{18}$$

$$\tilde{f}_i\langle v\rangle|_{x_0} = f_1|_{x_0} + df_i\langle v\rangle + O(\|v\|^2) \tag{19}$$

$$= f_1|_{x_0} + \sum_{j\neq 1} f_j\langle v\rangle \sum_k v_k c_{ijk}|_{x_0} + O(\|v\|^2) \tag{20}$$

The space of linear models for smooth frame fields is fully characterized by the elements of $c_{ij}$ of C, and can be generated from the first order terms of a Taylor series of $f_i$ centered at a point $x_0$. The first order approximation for the motion of a frame vector $f_i$ in a direction $v=\Sigma_k v_k f_k$ can be expressed as Equations (19) and (20) where we use the short-hand $c_{ijk}\equiv c_{ij}\langle f_k\rangle$ for the natural connections of the local frame. Since only 3 unique non-zero combinations of i, j are possible in $\Re^3$ due to the skew symmetry of C, there are only 9 unique non-zero combinations of $c_{ijk}$ possible for k=1, 2, 3. FIG. 9 illustrates the behavior of a frame field where each connection form predominates.

Considering the model at a point $x_0$ for all frame vectors and one-forms, an approximation of the frame from $F(x_0)$ to $F(x_0+v)$ can be obtained by the normalized model given in Equation (21) which in matrix notation yields Equation (22) where $C^i \in R^{3\times 3}$ denotes the matrix of connection forms with $c_{kl}{}^i = \epsilon_{jk} c_{kil}$ and $\epsilon_{ik}$-sgn(k−i). In general $\tilde{f}_1(v)$, $\tilde{f}_2(v)$, and $\tilde{f}_3(v)$ will not form an orthogonal basis. To establish we can combine Equation (15) with Equation (19) to yield Equation (23) for k≠i, k≠j.

$$\tilde{f}_i(x_o+v) = \frac{f_i + df_i\langle v\rangle}{\|f_i + df_i\langle v\rangle\|} \tag{21}$$

$$\tilde{f}_i(x_o+v) = \frac{f_i + FC^i F^T v}{\|f_i + FC^i F^T v\|} \tag{22}$$

$$f_i\langle v\rangle|_{x_0} \cdot f_i\langle v\rangle|_{x_0} = \begin{cases} 1 + c_{ij}^2 + c_{ik}^2 & :i=j \\ c_{ik} c_{jk} & :i\neq j \end{cases} \tag{23}$$

B2. Estimation of Connection Forms

The full space of linear models for smooth frame fields was introduced in Equation (20). It was found that this space has at most 9 independent parameters $c_{ijk}$ which fully characterize the local geometry of a frame field. Accordingly, we need to compute these parameters for a smooth frame field.

B2.1 Direct Computation of Connection Forms

The connection one-forms $c_{ij}$ can be directly obtained from the vector fields $f_i$ and their differentials $df_i$ using Equation (14) to yield Equation (24) and therein Equations (25) and (26). The differential $df_i$ can be computed by applying the exterior derivative of a function g: $R^n \to R$ as given in Equation (27) which yields Equations (28) to (30) where $$= \left[\frac{\delta x^i}{\delta x_j}\right] \in R^{3\times 3} J$$

is the Jacobian matrix of partial derivatives and ds=$(dx^1, dx^2, dx^3)^T$. Setting $v=f_k$ then we finally obtain Equation (31). The Jacobian matrix J can be approximated to first order using for example finite differences such that $$\frac{\delta f_{ij}}{\delta x_k}(x) \approx \frac{1}{2}(f_{ij}(x+e_k) - f_{ij}(x-e_k)).$$

$$df_i \cdot f_k = \left(\sum_j^3 c_{ij} f_j\right) \cdot f_k \tag{24}$$

$$= \sum_j^3 c_{ij} \delta_{jk} \text{ since } f_i \cdot f_k = \delta_{ik} \tag{25}$$

$$= c_{ik} \tag{26}$$

$$dg = \sum_i^n \frac{\delta g}{\delta x_i} dx^i \tag{27}$$

$$df_i \cdot f_j\langle v\rangle = \left(\sum_l^3 \left(\sum_k^3 \frac{\delta f_{ik}}{\delta x_k} dx^k\right) f_{jl}\right)\langle v\rangle \tag{28}$$

$$= f_j^T J(f_i) dx\langle v\rangle \tag{29}$$

$$= f_j^T J(f_i) v \tag{30}$$

$$c_{ijk} = df_i \cdot f_j\langle f_k\rangle = f_j^T J(f_i) f_k \tag{31}$$

B2.2 Computation Via Energy Minimization

The connection forms $c_{ijk}$ at a point $x_0$ can also be found as the minimizer of the energy contained within a neighbourhood $\Omega$ as established in Equation (32) where $\epsilon_i$ is a function of the error for each frame axis, as given by Equation (33) where $f_i(x_0+v)$ is the frame data term and $\tilde{f}_i(x_0+v)$ is its approximation using Equation (22).

$$c_{ijk}^*(x_0) = \underset{c_{ijk}}{\arg\min} \frac{1}{|\Omega|} \sum_{v\in\Omega} \sum_i^3 \varepsilon_i(x_0+v) \tag{32}$$

$$\varepsilon_i(x_0+v) = \arccos(f_i(x_0+v) \cdot \tilde{f}_i(x_0+v)) \tag{33}$$

Here, $\Omega$ can take any shape. We will denote a cubic isotropic neighborhood in $\Re^3$ of radius i as $\Omega_{2i+1}$, and 6 nearest neighbors will be denoted as $\Omega_3^+$. The optimization energy in Equation (33) can be solved for using standard algorithms such as Nelder-Mead and BOBYQA.

B2.3 Method Comparison

Figure 10:
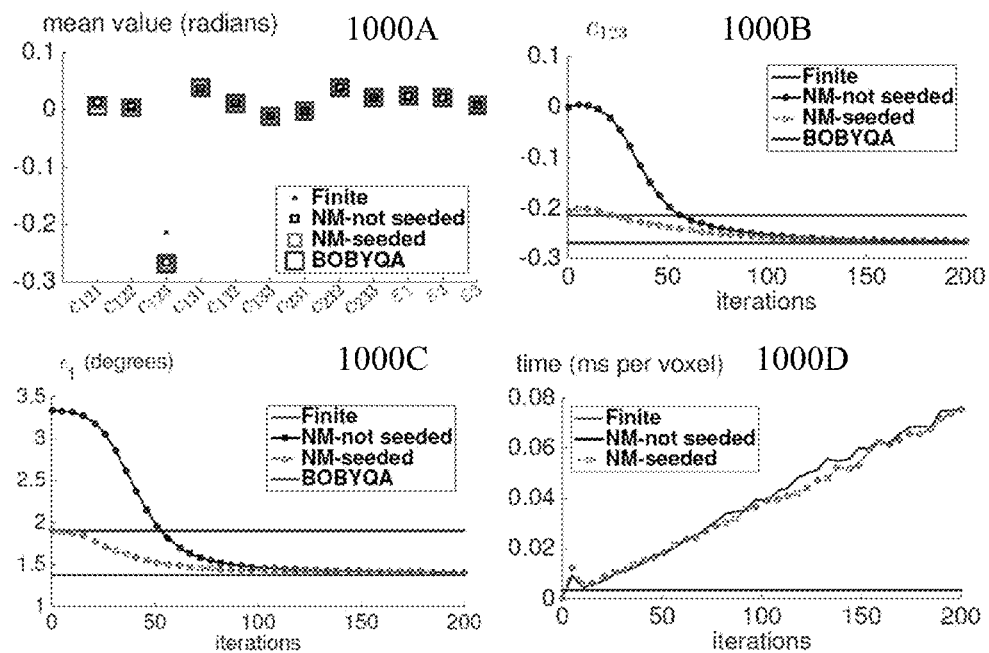
FIG. 10 depicts parameters after 200 Nelder-Mead iterations including convergence plots for $c_{123}$ and $\epsilon_1$ and computational timings for different estimation techniques.

Now referring to FIG. 10 there are compared mean connection form estimation results and timings for direct and optimized computations using a sample of a smooth frame field of biological (cardiac) nature containing 50,000 nodes. Here, all connection forms are estimated in a neighborhood $\Omega_3^+$ and then evaluated in $\Omega_3$. Finite difference computations of Section B2.1 are referred to as Finite, and Nelder-Mead computations as NM. Seeded computations make use of the results obtained using finite differences In general, unseeded computations systematically yield a larger error than seeded ones, but both eventually converge to the same error, at around 150 iterations, which requires about 3 seconds of computation time. In comparison, BOBYQA optimization takes about 1 minute to fully converge, and yields a slightly lower error than Nelder-Mead and finite computations. One major advantage of the BOBYQA optimizer is the possibility of enforcing bounds on the variables to fit, since it is a constrained optimization scheme. In general, bounds can be obtained on the values of the $c_{ijk}$ terms, based on both empirical and theoretical observations. In the discrete case for a smooth orthonormal frame field, and using a central differentiation scheme, the frame axis differential $df_i = d(f_{i1}e_1 + f_{i2}e_2 + f_{i3}e_3)$ in $\mathfrak{F}$ $f_i$ is bounded due to Equation (34).

$$\left|\frac{\delta f_i}{\delta x_k}\right|_x \approx \left|\frac{f_{ij}(x - e_k) - f_{ij}(x + e_k)}{2}\right| \leq 1 \qquad (34)$$

Using $\|\cdot\|_1$ to denote the Euclidean one-norm, then the bounds defined by Equations (35A) to (35C) are obtained.

$$|c_{ij}\langle v \rangle| = |f_j T \mathfrak{F} f_i(x_1, x_2, x_3)v| \qquad (35A)$$

$$\leq f_j T \cdot l[\|v\|_1 \|v\|_1 \|v\|_1]^T \qquad (35B)$$

$$\leq \| \|_1 \leq \alpha \text{ for } v \in \Omega_{2\alpha+1} \qquad (35C)$$

In certain applications where computation time is not an issue and where there is a prior on connection form bounds, the seeded BOBYQA optimization scheme may be preferable. For the remainder of this specification however, a Nelder-Mead optimization scheme running for 300 iterations will be assumed. The upper bound of Equations (35A) to (35C) will be enforced by discarding volume elements that fall outside of permitted values.

The Pointcaré-Hopf theorem states the existence of at least one singular point for frame fields embedded in surfaces with a non-zero Euler characteristic. An example is the singularity that naturally arises in the GHM. Whereas in theory characterizations of open sections on manifolds can be made free from singularities, in dealing with acquired or fitted data these could still arise due to the discretization of the underlying frame field. In applications such as the one discussed below in Section B4, singularities generate a sharp turning in the frame vectors. This behavior cannot be captured by the first order model of Equation (20) which will therefore only yield a coarse approximation. Using the direct computations of Equations (31), Equation (34) shows that connection forms will be bounded numerically near singularities. However, optimized computations may yield large values, in which case a hard threshold can be placed on Equation (32) or a regularization term can be added. These strategies should be seen as heuristics, and will in general not yield a good fit to the data close to singularities.

B3. Maurer-Cartan Embeddings

The geometrical intuition conveyed by the $c_{ijk}$ parameters in Equation (8) and illustrated in FIG. 9 can be used to develop local embeddings or connection form models. By imposing constraints on certain parameters, the shape and the complexity of the resulting frame field can be controlled explicitly. Given a seed frame $f_i(x_0)$ with known parameters $c_{ijk}$, the solution to the manifold $f_i(x)$ for all x can then be found by integration. In some cases, such as with the GHM as discussed below, there exist closed form solutions. In general, models may be solved for numerically by using Equation (22) in a standard integration scheme.

Now the inventors demonstrate embeddings based on generalized helicoids, and those which lie on spherical and ellipsoidal shells. The general case in which all connection forms are used will be referred to as the full connection form model, and the one where all connection forms are set to zero as the constant connection form model.

B3.1. Generalized Helicoids as Connection Forms

The model for representing the geometry of 3D smooth streamline flows within the prior art known as the Generalized Helicoid Model (GHM) is based upon modeling texture flows and has been used to measure axonal geometry in white matter fiber tracts and to characterize muscle directions in the heart by modeling the local variation of a smooth frame field. The inventors show in this section that the GHM model is a subset of Equation (22), where all but 3 parameters are zero.

$$f_1(x_0 + v) = \cos\theta f_1(x_0) + \sin\theta f_2(x_0) \qquad (36A)$$

$$\theta(x_0, v) = \arctan\left(\frac{K_1(x_0)v_1 + K_2(x_0)v_2}{1 + K_2(x_0)v_1 - K_1(x_0)v_1}\right) + K_3(x_0)v_3 \qquad (36B)$$

$$A(\theta) = \begin{bmatrix} \cos\theta & \sin\theta & 0 \\ -\sin\theta & \cos\theta & 0 \\ 0 & 0 & 1 \end{bmatrix} \qquad (37)$$

$f_1$ is given by the GHM vector field in Equations (36A) and (36B) where $\theta(x_0, v)$ parameterizes a minimal surface over parameter fields $K_i$ and where $v = \Sigma_i v_i f_i(x_0)$. The 9 parameters $c_{ijk}$ of Equation (22) can then be evaluated for $f_1$. The trivial basis $e = f_i(x_0)$ is chosen in order to construct the attitude matrix A, Equation (37), where $\theta = \theta(x_0, v)$. Since $f_1$ stays parallel to the tangent $f_1 - f_2$ plane at $x_0$ and $f_3$ remains unchanged, then $\hat{f}_2 = f_3 \times f_1$ will also stay parallel to that tangent plane at $x_0$, Hence, we must have $c_{13} = c_{23} = 0$ which is confirmed by straightforward computations. As a result the one-form is found to be defined by Equation (38) since the derivatives are to be evaluated at the origin, and where $K_i$ and $df_i$ are evaluated at $x_0$. Accordingly we arrive at Equation (39) and conclude that the GHM is a subset of Equation (22), where all but $c_{121}$, $c_{122}$, and $c_{123}$ are zero. As a result, in frame fields where the 6 connection forms $c_{13k}$, $c_{23k}$|$k \in \{1,2,3\}$ are non-zero, the GHM will not be able to comprehensively characterize the underlying geometry of the frame field. Further other issues can arise with the GHM since the rotation angle $\theta(x_0, v)$ yields a frame field singularity when Equation (30) is satisfied.

$$c_{12} = K_1 df_1 + K_2 df_2 + K_3 df_3 \qquad (38)$$

$$c_{12k} = c_{12}\langle f_k \rangle = K_k, k \in \{1, 2, 3\} \qquad (39)$$

$$v = \left(1 + \left(\frac{K_1}{K_2}\right)^2\right)^{-1} (-K_2, K_1, 0) \qquad (40)$$

B3.2 A Model on Spheres

Figure 11:
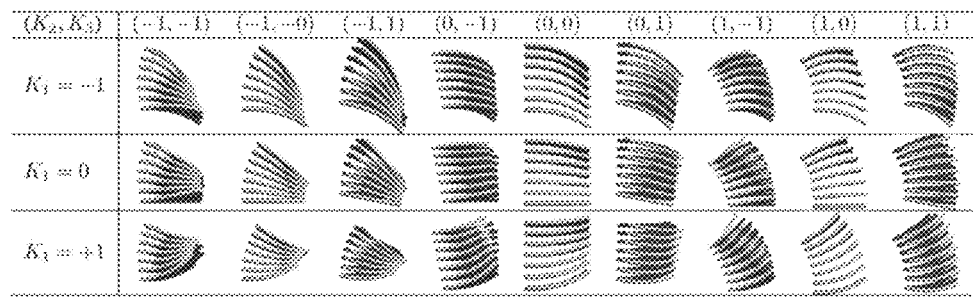
FIG. 11 depicts solutions for 3 neighboring spheres $\rho=1$, 1.15, 1.3 where $K_1$ models the turning towards the tangent vector $f_1$ and each column represents a distinct tuple of $(K_2, K_3)$ which expresses the turning of the tangent vector towards $f_2$ when moving along the $f_2$ (spreading) and $f_3$ (turning) directions.

Connection forms can be constrained to generate thin spherical shell embeddings. Given a smooth surface where $f_1$ and $f_2$ span the local tangent plane, then we can generate a family of subspaces that are non-intersecting along $f_3$, by setting $c_{12}\langle f_k \rangle_k$, $k \in \{1,2,3\}$ as given in Equations (41A) and (41B) where $K_i$: $\mathfrak{R}^3 \to \mathfrak{R}$ are any smooth functions. The remaining parameters control the motion of frames within parallel spherical surfaces. For a point x on a spherical shell with center at $$x_0 - \frac{1}{\rho} f_3$$

we then obtain Equations (42A) and (42B) respectively. This completely specifies the local linear model for spherical shells using Equation (20). By numerical integration we can generate flow lines of $f_1$ in a local neighborhood, as illustrated in FIG. 11.

$$c_{12}\langle f_1 \rangle = K_1 c_{12}\langle f_2 \rangle = K_2 c_{12}\langle f_3 \rangle = K_3 \quad (41A)$$

$$c_{13}\langle f_3 \rangle = 0 c_{23}\langle f_3 \rangle = 0 \quad (41B)$$

$$c_{13}\langle f_1 \rangle = \frac{1}{\rho} \quad (42A)$$
$$c_{13}\langle f_2 \rangle = 0$$
$$c_{23}\langle f_1 \rangle = 0 \quad (42B)$$
$$c_{23}\langle f_2 \rangle = \frac{1}{\rho}$$

$$\begin{bmatrix} x \\ y \\ z \end{bmatrix} = \begin{bmatrix} \rho\cos(\phi)\sin(\psi) \\ \rho\sin(\phi)\sin(\psi) \\ \rho\cos(\psi) \end{bmatrix} \quad (43)$$

Figure 12:
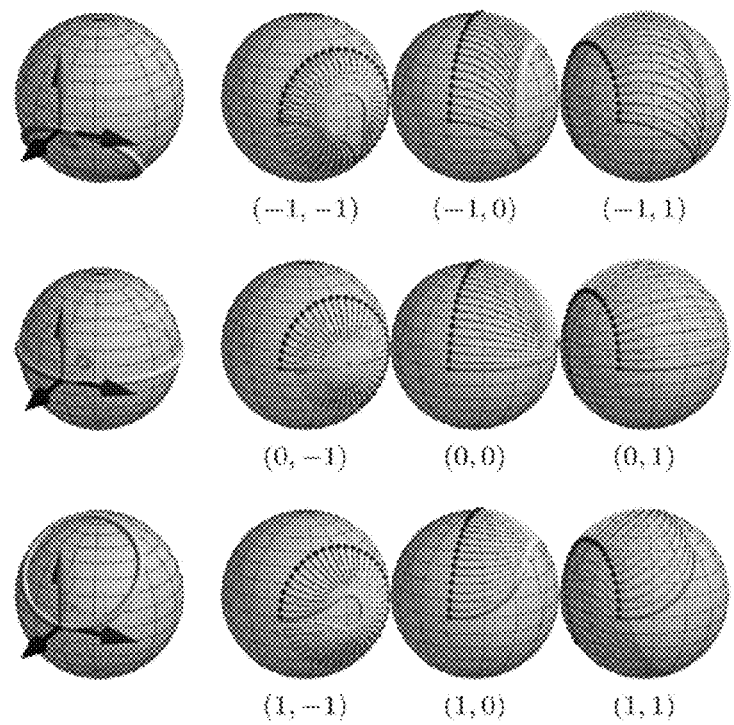
FIG. 12 depicts solutions to Equations (41) and (42) on the unit sphere, with initial frames are shown with column 1 depicts a single flow line whilst columns 2-4 show neighbouring flow lines from an initial starting point for various $(K_1, K_2)$ tuples.

Curves with $f_1$ as their tangent lie on a single shell and each forms a circle, as shown in FIG. 12. To prove that flow-lines of $f_i$ form circles on a sphere, consider a sphere in polar representation as given by Equation (43) centered at 0 and with radius $\rho$, and consider the intersection with a plane orthogonal to the z-axis of height $-\rho \le z_0 \rho$. Since $z_0 = \rho \cos(\psi)$, using Equation (43), the curve of intersection is found to be $$\rho = \left[ \sqrt{\rho^2 - z_0^2} \cos\phi, \sqrt{\rho^2 - z_0^2} \sin\phi, z_0 \right]^T,$$

which is a circle of radius $R = \sqrt{\rho^2 - z_0^2}$ with the z-axis as the axis of rotation. Evaluating the Maurer-Cartan form of a frame field, where $$f_1 = \frac{\partial_\phi p}{\|\partial_\phi p\|}, f_3 = \frac{(x, y, z)^T}{\|(x, y, z)^T\|},$$

and $f_1 = f_3 \times f_1$, we find that $c_{12}\langle f_1 \rangle = z_0/\sqrt{\rho^2 - z_0^2}$, $c_{13}\langle f_1 \rangle = -1/\rho$ and $c_{23}\langle f_1 \rangle = 0$ which exactly corresponds to the constraints given by Equations (41A)-(41B) and (42A)-(42B) when $K_1 = z_0/\sqrt{\rho^2 - z_0^2}$. To align the two coordinate systems, we first set the tangent of the circle to be $f_t$, and set the change of $f_t$ in the direction $f_t$ to be the normal to the circle. The normal is then derived directly from Equations (22), (41A)-(41B) and (42A)-(42B) as the unit vector parallel to $df_1\langle f_1 \rangle = K_1 f_2 - (1/\rho) f_3$. Finally, the radius of the circle is found by solving for $z_0$ in terms $K_1$, $z_0 = \pm K_1 \rho^2/\sqrt{1+K_1^2 \rho^2}$ and inserting this into R which yields $R = \rho/\sqrt{1+K_1^2 \rho^2} = 1/|df_1\langle f_1 \rangle|$.

B3.3 A Model on Ellipsoids

The spherical embedding of Section B3.2 is a specialization of ellipsoidal geometry. In the general case, manifolds are embedded within thin ellipsoidal shells, which we refer to as homeoids. Given any smooth surface with anisotropic principal curvatures, and where $f_1$ and $f_2$ span the tangent plane which is organized in thin shells, then Equations (41)-(41B) and (42A)-(42B) generalize to Equations (44A) and (44B).

$$c_{13}\langle f_1 \rangle = \frac{1}{\rho_1} \quad (42A)$$
$$c_{13}\langle f_3 \rangle \ne 0$$
$$c_{23}\langle f_3 \rangle \ne 0 \quad (42B)$$
$$c_{23}\langle f_2 \rangle = \frac{1}{\rho_2}$$

Figure 13:
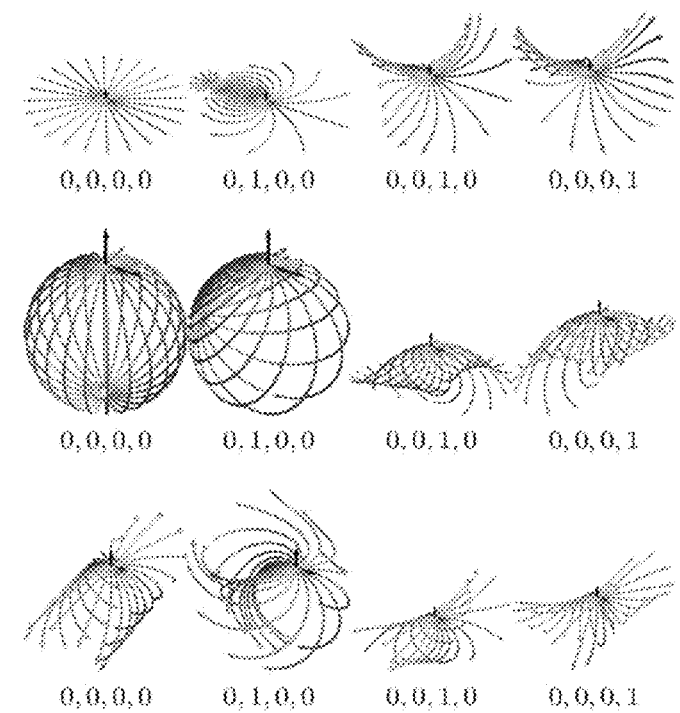
FIG. 13 depicts examples of ellipsoidal solutions integrated from a flat patch (first row), a spherical patch (second row), and a cylindrical patch (third row) for various values of $c_{131}$, $c_{132}$, $c_{231}$, $c_{232}$.

Here, $c_{13}\langle f_3 \rangle$ and $c_{23}\langle f_3 \rangle$ are only zero when $f_1$ and $f_2$ are aligned with the principal directions of the underlying surface. This completely specifies the local linear model for elliptical shells using Equation (22). As for the spherical shell model, flow lines can be generated in a local neighbourhood by numerical integration. However, these yield a more complex geometry, as illustrated in FIG. 13, for frame integrations on various surfaces: a flat, a spherical, and an ellipsoidal surface.

B4. Application to Myofiber Geometry

The walls of the ventricles in the mammalian heart are composed of elongated muscle cells called cardiomyocytes, which are densely packed within a collagen matrix. This matrix forms the bulk of the heart, which has a truncated ellipsoidal shape. Cardiomyocytes stack approximately end on end, forming smoothly varying structures known as myofibers. The arrangement of myofibers is critical for normal heart function because it is the alternate contraction and relaxation along their length that determines pumping efficiency Accordingly, in this section the inventors apply connection form based modeling to characterize myofiber geometry. This could have many practical uses including differentiation between normal and pathological arrangements, integration of myofiber geometry into patient-specific cardiac models and monitoring changes in heart wall structure in studies of development and aging.

Figure 14:
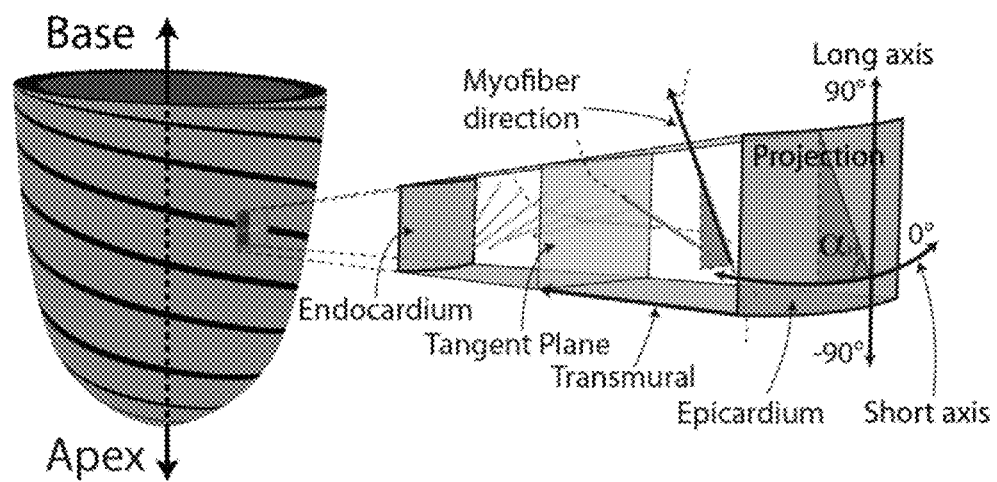
FIG. 14 depicts the helix angle definition employed within the specification.
Figure 15:
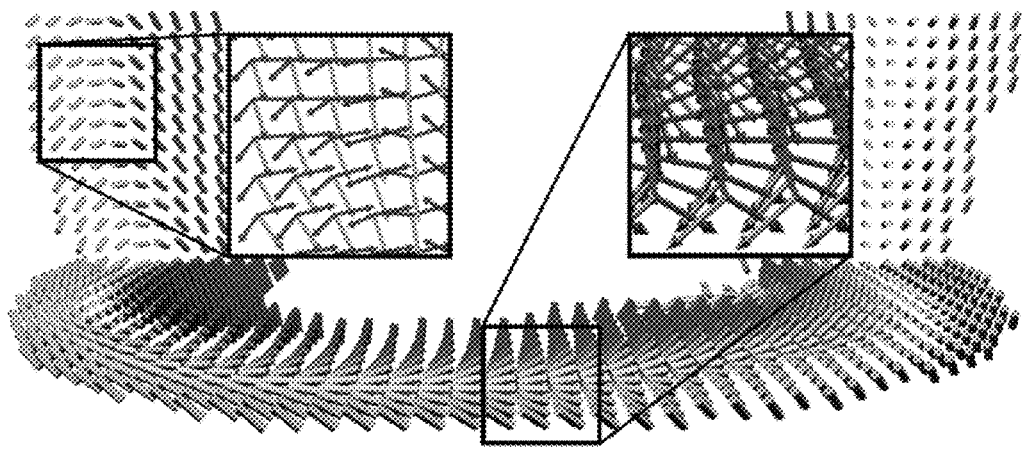
FIG. 15 depicts the principal fiber direction and cardiac frame fields for a rat heart obtained from dMRI data.

Early work based on histology has shown that cardiac myofibers are locally aligned to helical curves which wrap around the ventricles. Various models have been proposed to explain this organization, based on both physical and mathematical considerations. Also, more recently it has become possible to study this organization within the intact myocardium using diffusion magnetic resonance imaging (dMRI). In analyses of myofiber geometry, the helix angle, taken to be the angle between the fiber direction projected onto a plane orthogonal to the penetration direction and the short-axis plane (see FIG. 14), is ubiquitous. Several accounts from both small-scale histology and voxel-scale studies using dMRI report that along a transmural penetration line from the heart's outer to inner wall, the helix angle varies smoothly and regularly, undergoing a total change in orientation of about 120° in mammals. The variation in helix angle provides a coarse description of fiber geometry, which in turn depends on the choice of penetration direction, as illustrated in FIG. 15. The methods developed in the previous section have the potential to provide more complete local characterizations of heart wall myofiber geometry.

The scale of current dMRI measurements is at least one order of magnitude larger than the length of individual cardiomyocytes and thus the diffusion signal reflects properties of a fibrous composite. Modeling myofiber geometry within the prior art using the GHM as described supra to parametrize myofiber orientation in the heart wall has been performed in three mammalian species, the rat, the canine, and the human. A limitation of using the GHM is that its flow lines are constrained to lie on planar manifolds, in spite of the curvature of the heart wall evident in FIG. 14. This limitation allows only three available geometrical parameters, resulting in a reduced ability for characterizing increasingly larger and complex myofiber neighborhoods. Accordingly, the inventors have instead established a methodology of fitting a frame field to cardiac dMRI data and to then examine its connection forms.

The inventors describe below this analysis to a diffusion MRI database of healthy rat hearts, containing 8 rat subjects, which will be labeled as subjects A to H, with $(0.25 \text{ mm})^3$ voxel resolution and a dimension of 64×64×128 voxels.

B4.1 Selecting a Cardiac Frame Field

Cardiac diffusion MRI volumes are sampled on 3D rectangular lattices with coordinates $x=\Sigma x_i e_i$, $x_i \epsilon Z^3$. In order to apply connection form analysis, a local cardiac frame needs to be defined. The first frame vector of this frame is chosen to be parallel to the orientation of the principal direction of diffusion $u_1$, i.e. $f_1 \backslash\backslash u_1$. Because the direction of $u_1$ is locally ambiguous, our first task is to enforce consistency in the direction of $f_1$ among voxel neighbors. This is done using an adaptive cylindrical coordinate system. The centroid $c_z$ of the chamber within each short-axis slice mask $\xi_z$ is first determined using Equation (45). $f_1$ is then locally made to turn clockwise with respect to that centroid for each slice $\xi_z$, and for all $x \epsilon \xi_z$ as given by Equations (46) to (48) where $l_z$ is the local approximation to the heart's long-axis. For most hearts under consideration, $l_z$ approximately coincides with the volume's z axis.

$$c_z = \frac{\sum_{x \in \xi_z} x}{|\xi_z|} \quad (45)$$

$$l_z = \frac{c_{z+1} - c_{z-1}}{\|c_{z+1} - c_{z-1}\|} \quad (46)$$

$$f_1(x) = \text{sign}((u_1(x) \times (x - c_z) \cdot l_z)) u_1(x) \quad (47)$$

$$f_1(x) = v_x(u_1) u_1 \quad (48)$$

We now need one additional orthogonal frame axis to $f_1$ in order to define a frame field. In fact, since we require $f_i \epsilon R^3$ to have unit length, only one additional degree of freedom is required to fully describe a frame field: a rotation about $f_1$. In principle, any model for this rotation could be adopted, based on geometrical intuition, biological relevance, or computational considerations. However, in common with conventional cardiac spatial analysis, the inventors use a model for the frame field which is based on an estimate of the local normal to the heart wall. The normal is approximately the direction in which the endocardium moves when the heart beats, which is also naturally orthogonal to local myofiber orientations, and thus is biologically meaningful, This also leads to a consistent choice of the remaining frame field directions throughout the heart wall, and a smooth rotation of the frame field from one voxel to its neighbor.

Figure 16:
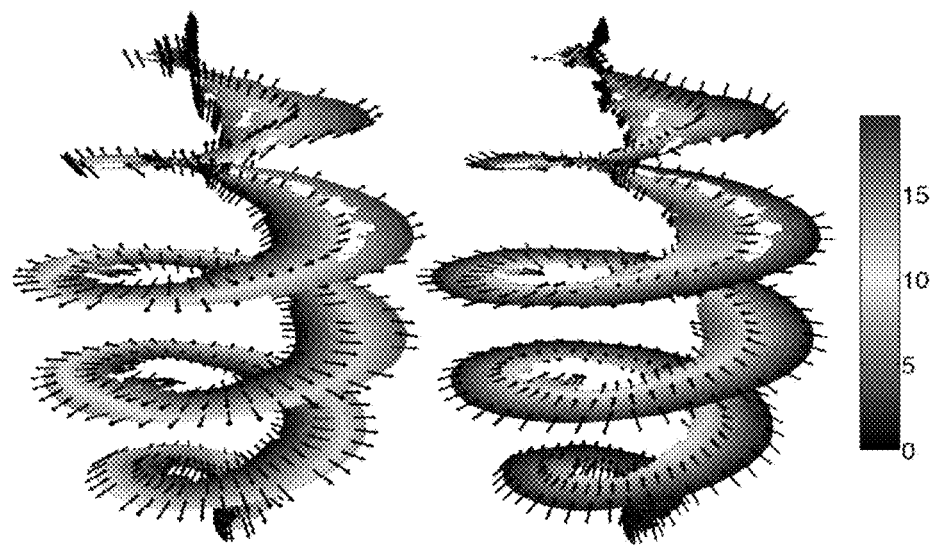
FIG. 16 depicts endocardium (left) and epicardium (right) Euclidean distance, ranging from zero to 20 voxels and distance gradient vectors.

Specifically, we first estimate a transmural direction $\hat{f}_3$ using the gradient vector of a distance transform produced as follows:

the binary image (mask) of the heart is closed using mathematical morphological operations;

the Euclidean distance to the heart wall is evaluated at every point to both the epicardium and endocardium (see FIG. 16), and the endocardium gradient is negated and the average of the two gradients is then computed.

The normals $\hat{f}_3$ are then aligned to point from outer to inner wall. With $f_1$ and $\hat{f}_3$, a local frame is specified at x in Equations (49A)-(49C) where $f_3$ is the part of $\hat{f}_3$ orthogonal to $f_1$. The local plane spanned by $f_1$ and $f_2$ will be referred to as the tangent plane. FIG. 15 shows a sample of this frame field within two cross-sectional cardiac slices. Near structural boundaries, and due to various anomalies, discontinuities may arise in the frame field. This is typically not observed due to biology and is due to the inherent smoothing of the diffusion signal. Various heuristics could be used to identify and mask out these locations, for example using Equation (35).

B4.2 Cardiac Maurer-Cartan Connections

Figure 17:
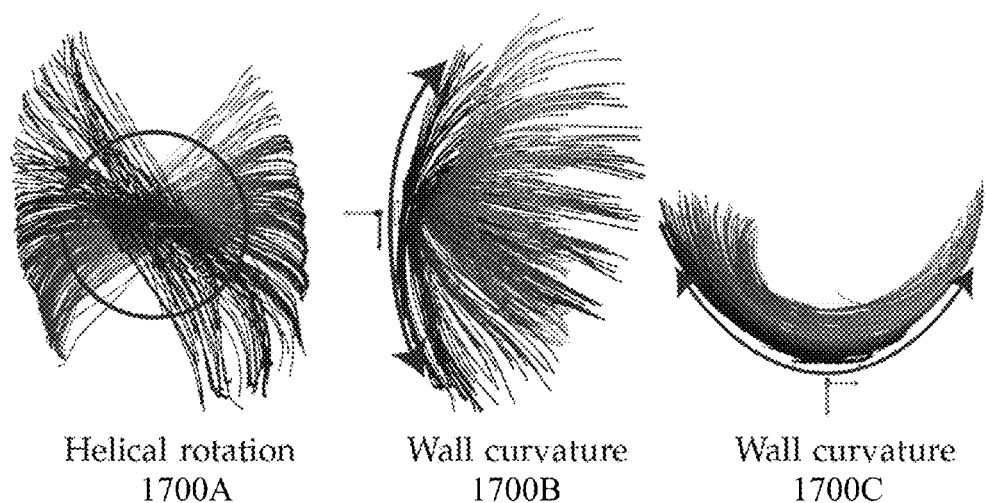
FIG. 17 depicts flow lines in the myocardium, found by tracking the first eigenvector of diffusion wherein a frame indicates the axial plane of the heart, the transmural direction, and the direction from the base to the apex.

The inventors now employ the Maurer-Cartan connection forms to analyse the cardiac frame field. To get a preview of the biological relevance of this methodology FIG. 17 illustrates the correspondence between three large-scale geometrical features exhibited by cardiac fibers and connection forms, namely, the variation of the helix angle is related to $c_{123}$, the short-axis curvature of the heart wall to $c_{131}$, and the long-axis curvature to $C_{232}$.

B4.2.1 Cardiac Moving Frame Intuition

Considering the frame at $x_0$, one-form contractions $c_{ijk}$ can be interpreted as the amount of turning of $f_i$ towards $f_j$, when considering neighboring frames in the direction $f_k$. The rotations of $f_1$ towards $f_2$, $c_{12}\langle f_k \rangle$, are intimately linked to the curvature parameters of the GHM. These rotations intuitively describe the manner in which myofibers turn in the tangent plane of the heart, $c_{121}$ in first image 900A in FIG. 9, describes their tangential curvature, $c_{122}$, shown in first image 900B in FIG. 9, their fanning in the tangent plane, and $c_{123}$, shown in third image 900C in FIG. 9, their transmural turning or equivalently the rate of change of the helix angle. The rotations of $f_1$ towards $f_3$, $c_{13}\langle f_k \rangle$, express the turning of the fibers towards the inner wall:

$c_{131}$ is related to a sectional curvature of the heart wall in the tangential direction, fourth image 900D in FIG. 9;

$c_{132}$ describes an upwards twisting of the tangent plane and the rate of change of the transverse angle, fifth image 900E in FIG. 9; and $c_{133}$ describes the degree of transmural fanning of the local fiber population away from or towards the tangent plane, sixth image 900F in FIG. 9.

For the remaining rotations:

$c_{231}$ measures twisting of the tangent plane, seventh image 900G in FIG. 9;

$c_{232}$ is related to a second sectional curvature of the heart wall, eighth image 900H in FIG. 9; and $c_{233}$ measures myofiber fanning (in or out) in the transmural direction, ninth image 900I in FIG. 9.

B4.2.2 Full Volume Histograms

Figure 18:
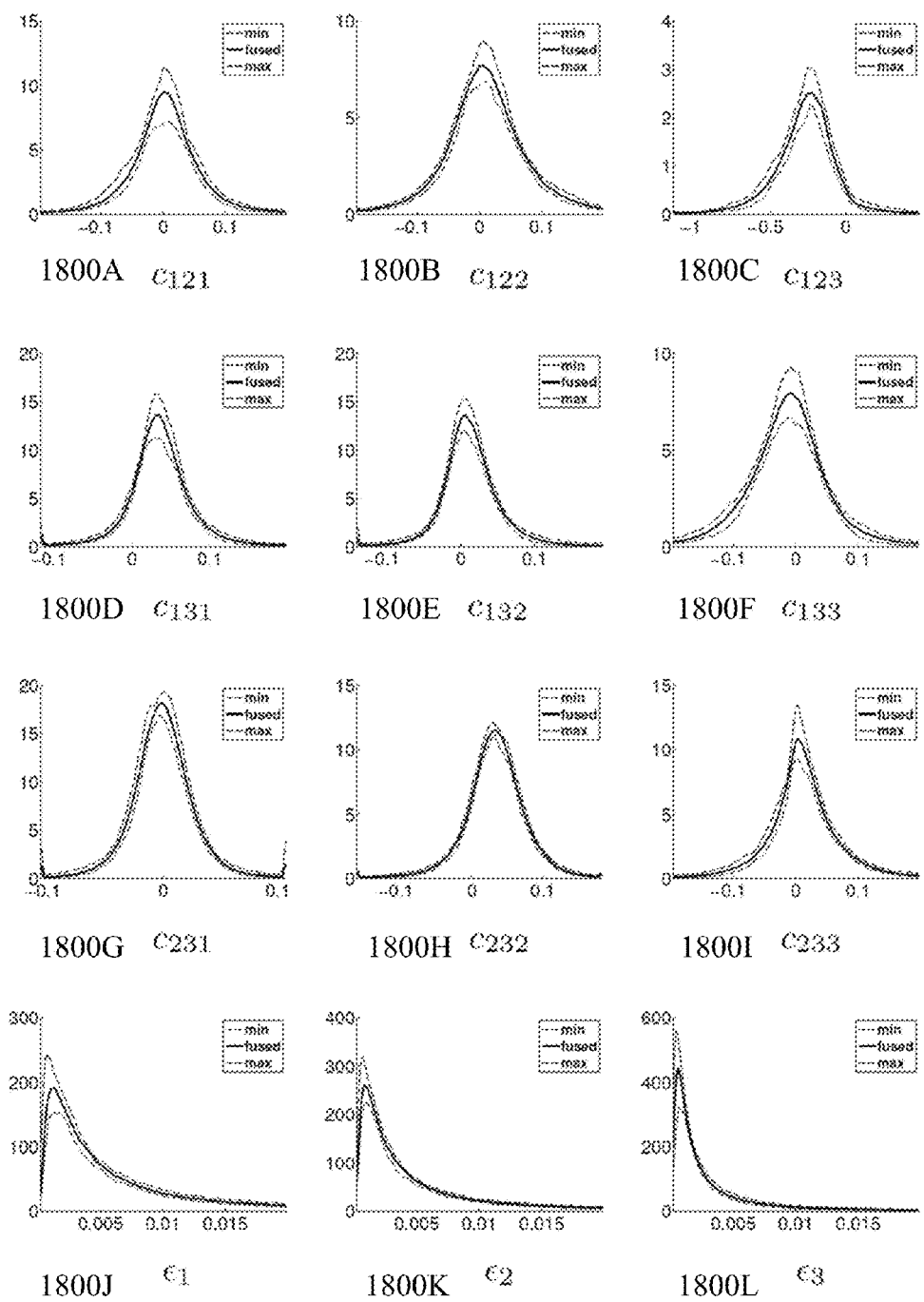
FIG. 18 depicts volume histograms of $c_{ijk}$ connections (radians/voxel) and fitting errors (radians) for $\Omega_3$ by fusing all rats in the dataset using optimized parameter computations together with the minimum and maximum dataset envelope for each value.

Full volume histograms for optimized $c_{ijk}$, computations in $\Omega_3$ are shown in FIG. 18 for each subject in the dataset. The histograms show that connection forms, in particular the variation of the helix angle $c_{123}$, are globally consistent among different healthy subjects of the same population. These connection histograms could be used for studying various cardiomyopathies in place of focusing solely on the helix angle. The latter cannot be used for detecting or surgically restoring anomalies such as myocardial infarction and hypertrophy. For example, in hypertrophic hearts the myocardium becomes more spherical globally; using our framework, this should result in sharper histograms for the sectional descriptors $c_{131}$ and $c_{232}$. Other cardiomyopathies that are more localized could be investigated from the local geometrical signature of the cardiac frame field.

Figure 19:
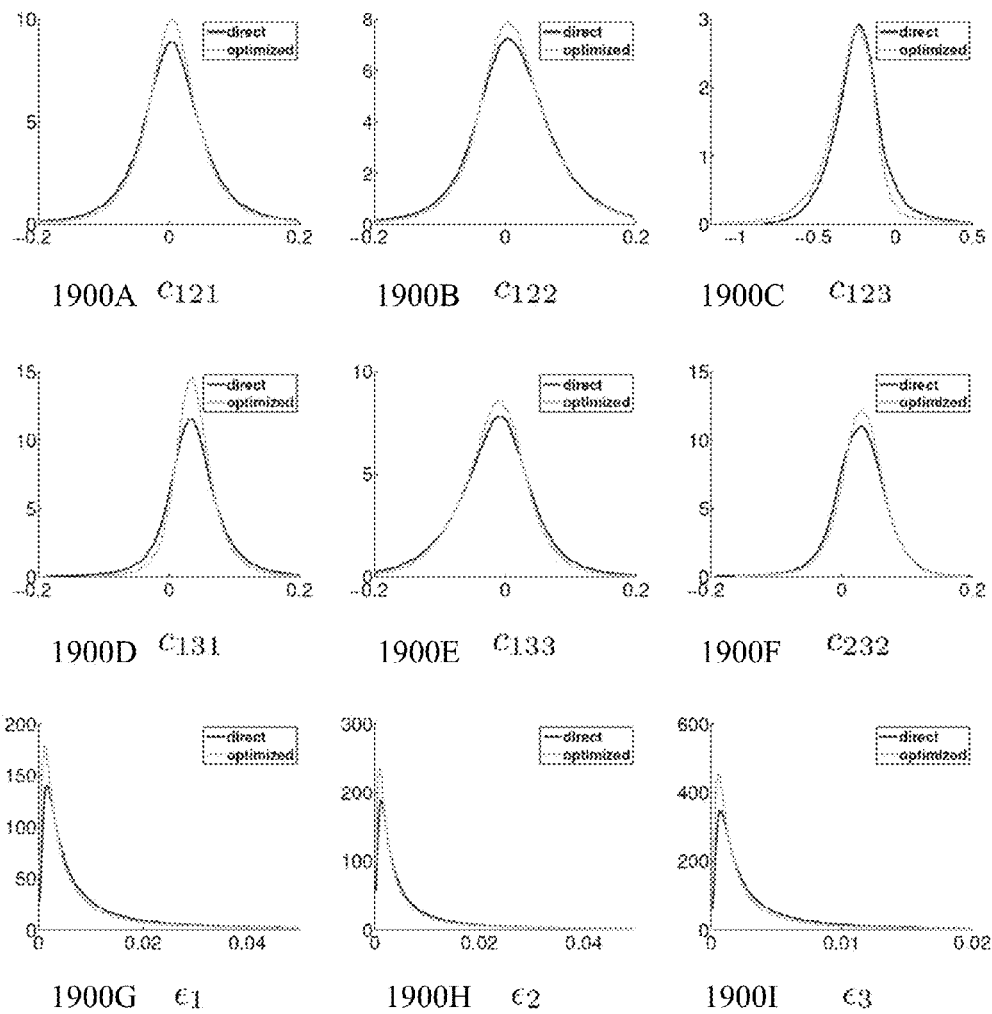
FIG. 19 depicts selected dataset volumes of rat connection forms $c_{ijk}$ (radians/voxel) and fitting errors $\epsilon_i$ (radians) in $\chi_3$ for the optimized and direct computations.

A comparison of selected volume histograms for the direct and optimized parameter estimation methods in $\Omega_3$ is shown in FIG. 19. As expected, optimized computations converge near values obtained by the direct computations while lowering the fitting error. Further spatial analysis in Section B4.3 (Table 3) supports these observations.

B4.2.3 Transmural Histograms

Figure 20:
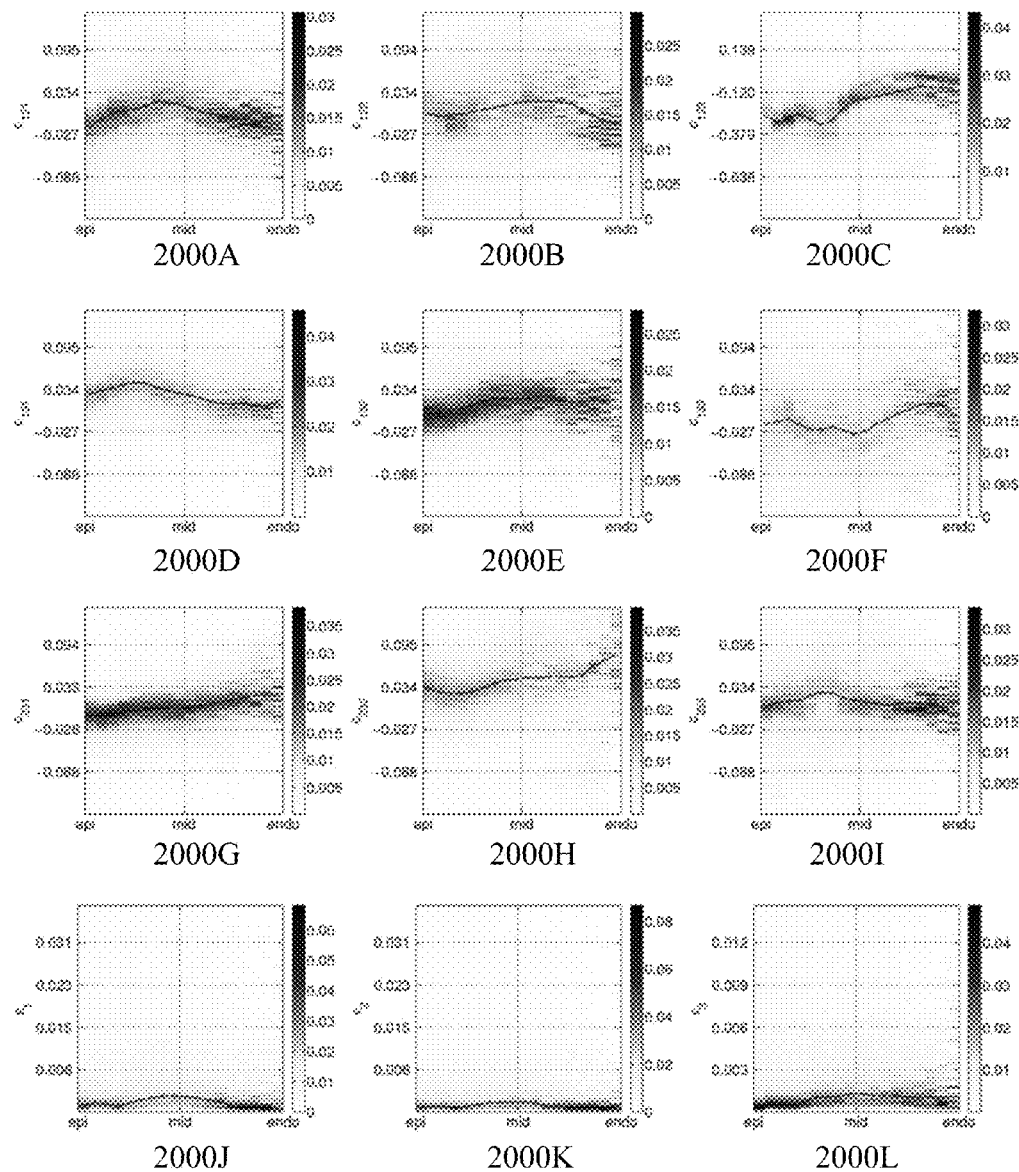
FIG. 20 depicts transmural histograms of combined volumes of $c_{ijk} \equiv c_{ij} \langle f_k \rangle$ and fitting errors in $\Omega_3$ for the rat data sets using optimized parameter computations.

Now referring to FIG. 20 there are depicted the results of sampling the 9 connection forms $c_{ijk}$ throughout the cardiac wall based on distance to the epicardium. A normalized marginal histogram is obtained for each distance by sampling all voxels that correspond to a given value of the distance transform in FIG. 16. Because of the exploratory and novel nature of these distributions, only a preliminary interpretation can be made of their shape. Any anatomical explanation for these variations is subject to errors in the segmentation (e.g. near the septum and within the right ventricle) as well as boundary effects near the walls which tend to spread out the distributions. In particular, the $c_{123}$ histogram shows that the course of the cardiac helix angle undergoes a major transition near the mid-wall. In general, connection forms are quite variable transmurally. An exact spatial localization and biological explanation of these variations is not the subject of this specification. By looking at spatial and scale dependence of the connection forms in the following section, we can however gain insight into the large-scale architecture of the cardiac frame field and answer some of these questions, B4.3 Scale and Spatial Dependence The direct computations of connection forms described in Section B2.1 depend only on the nature of the differential kernel used. On the other hand, the optimized parameter computations of Section B2.2 depend on the size and shape of the neighborhood $\Omega$ in which the energy (Equation (32)) is computed. $\Omega$ can be adjusted, and a filtering of the principal direction of diffusion can be performed to better target the scale of features that are to be extracted. This section thus investigates some of the possibilities in shaping the differentiation kernel for filtering and in selecting the energy neighborhood for computing the 9 $c_{ijk}$ connection forms using different isotropic neighborhoods $\Omega_i$. In doing so, we can measure the smoothness of the frame field, and obtain a preliminary spatial localization of its geometrical variation.

B4.3.1 Neighborhood Shape

Table 2 shows the mean and standard deviation for all voxels of the dataset, for each connection form and various neighborhoods $\Omega_i$. Fitting errors $\epsilon_i$ of Equation (33) are shown for the full connection form embedding. The results indicate globally stable mean values, although a local spatial analysis should be investigated to draw further conclusions. All errors increase following neighborhood size, meaning that increasingly more information is lost to the nonlinear $\theta(\|v\|^2)$ term in Equation (19). This indicates that a first-order linear model of the natural cardiac frame field is not practical to describe variability beyond a few voxels, given the current resolution at which the data was acquired.

TABLE 2

Effect of Neighbourhood Size on Optimized Connection Forms and Fitting Errors

| $\Omega$ | 3 | 5 | 7 |
|---|---|---|---|
| $c_{121}$ | 0.008 ± 0.083 | 0.010 ± 0.113 | 0.013 ± 0.202 |
| $c_{122}$ | 0.015 ± 0.091 | 0.022 ± 0.113 | 0.035 ± 0.244 |
| $c_{123}$ | −0.284 ± 0.237 | −0.304 ± 0.236 | −0.310 ± 0.313 |
| $c_{131}$ | 0.039 ± 0.043 | 0.040 ± 0.030 | 0.040 ± 0.029 |
| $c_{132}$ | 0.016 ± 0.047 | 0.016 ± 0.032 | 0.012 ± 0.034 |
| $c_{133}$ | −0.017 ± 0.063 | −0.017 ± 0.047 | −0.014 ± 0.038 |
| $c_{231}$ | 0.000 ± 0.032 | 0.001 ± 0.022 | −0.000 ± 0.018 |
| $c_{232}$ | 0.031 ± 0.046 | 0.028 ± 0.031 | 0.025 ± 0.024 |
| $c_{233}$ | 0.013 ± 0.074 | 0.010 ± 0.053 | 0.005 ± 0.042 |
| $\epsilon_1$ | 0.014 ± 0.030 | 0.029 ± 0.042 | 0.047 ± 0.053 |
| $\epsilon_2$ | 0.013 ± 0.028 | 0.027 ± 0.040 | 0.046 ± 0.051 |
| $\epsilon_3$ | 0.005 ± 0.014 | 0.009 ± 0.014 | 0.013 ± 0.015 |

Figure 21:
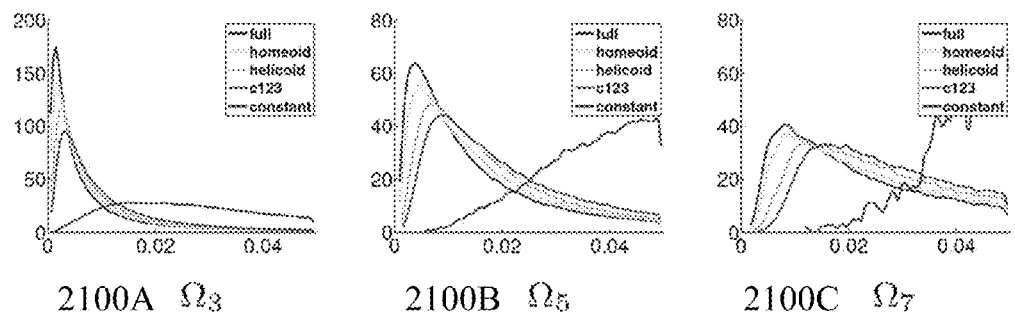
FIG. 21 depicts normalized distributions of the extrapolation error $\epsilon_i$ (in radians) for different neighborhoods $\Omega_i$.

FIG. 21 explores the relationship between neighborhood size and the various embeddings of Section B3. Extrapolation errors increase with increasing $\Omega_i$, similarly for all embeddings This linear relationship among different embeddings arises from the fact that most of the frame field variability is captured by the $c_{123}$ connection, which is considered in each embedding (with the exception of the constant model), and that added complexity does not proportionally contribute to a diminishing energy measure in Equation (33), a relationship that will be investigated in Section B4.4.

B4.3.2 Filtering Diffusion Directions

Filtering of diffusion directions after adopting cylindrical consistency using Equation (36) can be applied to compensate for the effect of noise in the diffusion volumes and to investigate the scale of fine muscle cardiac structures. In the context of cardiac tissue, whereas the principal direction of diffusion is widely accepted as corresponding to the orientation of cardiomyocytes, the second and third eigenvectors exhibit a high degree of spatial variability and their relationship to biology is not fully established. Thus, in the following description the inventors opt for a much simpler smoothing strategy, one that focuses on the first principal direction of diffusion only. The method we employ is based on an element-wise iterative normalized convolution with a Gaussian kernel $G_{\sigma^+}$, with standard deviation $\sigma^+$ on the vector field $f_1$ with a renormalization step, before computing the connection forms. The following update equation is $f_1^0 \equiv f_1$, $f_1^{n+1} = G_{\sigma^+} * f_1'' / \|G_{\sigma^+} * f_1''\|$. The remaining fields $f_2$ and $f_3$ are then obtained using Equation (45). The inventors make use of the notation $\sigma = \sigma^+ \sqrt{n}$ to denote n iterations of standard deviation $\sigma^+$.

Figure 23:
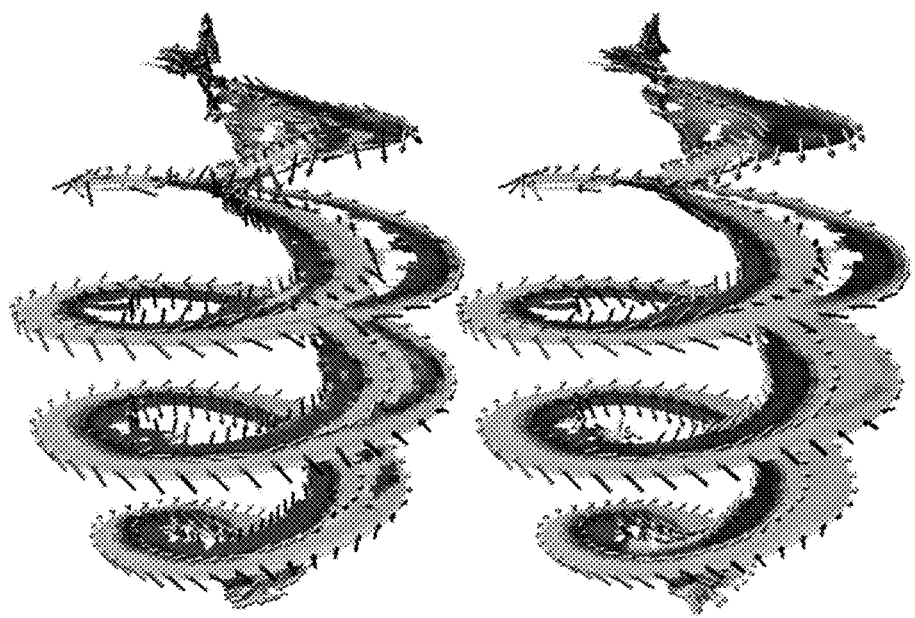
FIG. 23 depicts selected fiber directions $f_1$ for the rat A, before (left) and after (right) applying iterative filtering.
Figure 22:
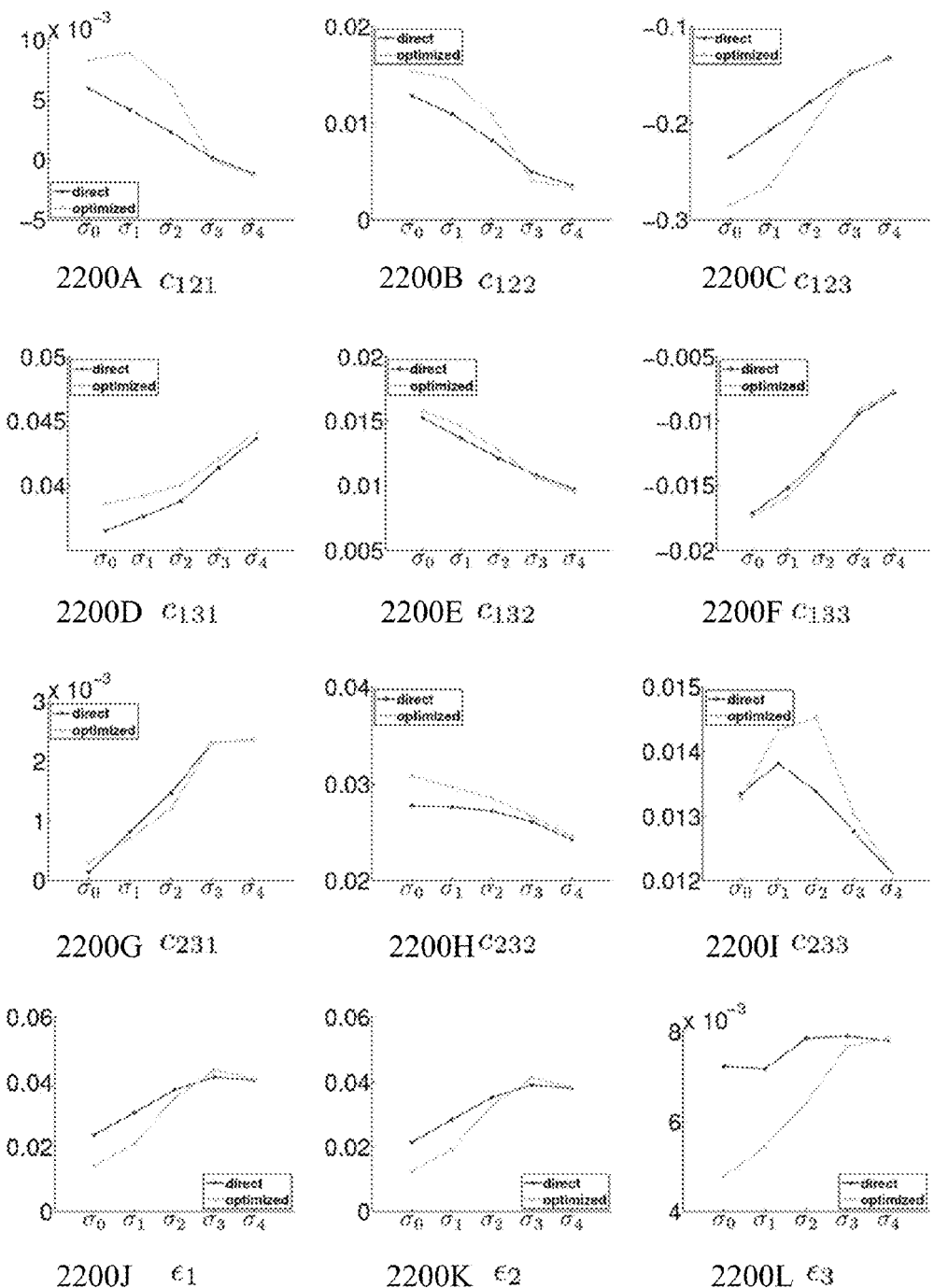
FIG. 22 depicts a method comparison and effect of $f_1$ filtering on mean $c_{ijk}$ and $\epsilon_i$ in the $_1$ for different standard deviations of the vector field $f_1$.
Figure 24:
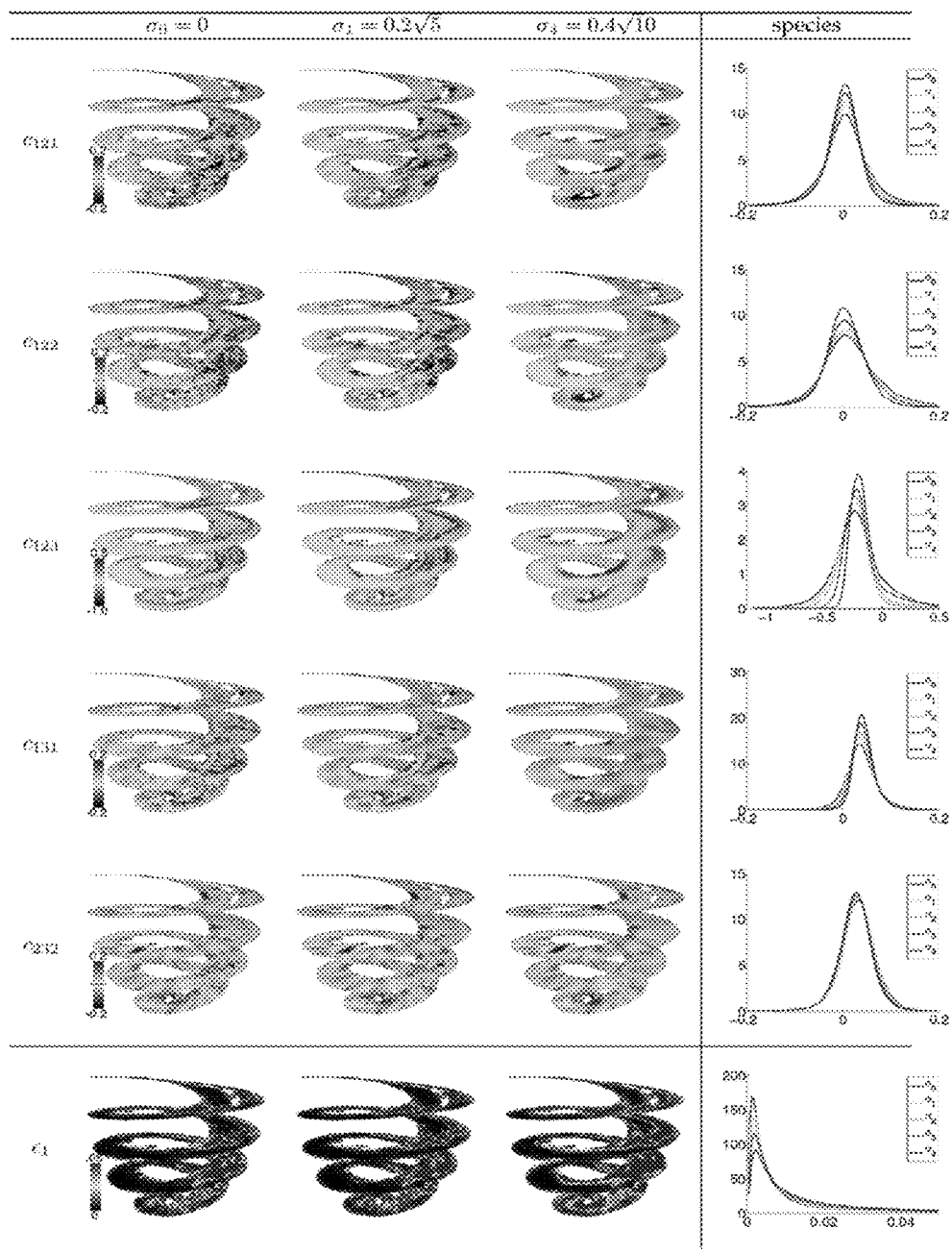
FIG. 24 depicts the effect of $f_1$ filtering on selected connection forms (rads/voxel) and extrapolation error $\epsilon_i$ (rads) wherein selected short-axis slices are shown in columns 1 to 3 for the rat subject A, and a full volume histogram is shown for the species in column 4.

As an example, FIG. 23 shows the effect of filtering on $f_1$ for $\sigma = 0.4\sqrt{10}$. FIG. 24 shows a volumetric helical sampling of selected connection forms and fitting errors, computed with respect to the unfiltered data, for various filtering magnitudes $\sigma_i$. As connection forms become smoother following an increase in filtering magnitude, geometrical measurements are obtained which pertain to large scale myofiber arrangements rather than local ones. Although the vast majority of errors are small (less than 0.05 radians), the last row shows that the fitting error is higher near the right ventricle, which is in part due to an incorrect labeling of background or interior voxels as lying within the myocardium. As a consequence, as $\sigma_i$ is increased values in these regions are propagated to their neighbors and are largely responsible for the overall increase in fitting error. In particular, for $c_{123}$ at $\sigma_4 = 0.4\sqrt{10}$ there is a false suggestion that the voxels turn in a clockwise direction in these mislabeled regions. FIG. 22 and Table 3 summarize these results as means over all volumes for each connection form and fitting error.

typical heart from the dataset, the average transmural depth from apex to sub-atria amounts to about 7 voxels. Integrating $c_{123}$ throughout this distance produces a total change of $-116.3°$, which is in close correspondence with values of $120°$ reported in the literature.

TABLE 3

Effect of Iterative Gaussian Smoothing Applied to $f_1$ on Extrapolation Error for Direct an Optimised Parameter Computations in $\Omega_3$

| | $\sigma = 0$ | | $\sigma = 0.2\sqrt{10}$ | | $\sigma = 0.4\sqrt{10}$ | |
|---|---|---|---|---|---|---|
| | Direct | Optimised | Direct | Optimised | Direct | Optimised |
| $c_{121}$ | .006 ± .078 | .008 ± .083 | .002 ± .076 | .006 ± .097 | −.001 ± .047 | −.001 ± .053 |
| $c_{122}$ | .013 ± .086 | .015 ± .091 | .008 ± .086 | .011 ± .103 | .044 ± .046 | .003 ± .047 |
| $c_{123}$ | −.235 ± .183 | .284 ± .237 | −.178 ± .232 | −.205 ± .271 | −.133 ± .163 | −.135 ± .169 |
| $c_{131}$ | .037 ± .054 | .039 ± .043 | .039 ± .040 | .040 ± .036 | .044 ± .026 | .044 ± .028 |
| $c_{132}$ | .015 ± .055 | .016 ± .047 | .012 ± .044 | .013 ± .040 | .010 ± .029 | .009 ± .031 |
| $c_{133}$ | −.017 ± .072 | .017 ± .063 | −.013 ± .067 | −.013 ± .056 | −.008 ± .045 | −.008 ± .044 |
| $c_{231}$ | .000 ± .034 | .000 ± .032 | .001 ± .032 | .001 ± .029 | .002 ± .029 | .002 ± .031 |
| $c_{232}$ | .028 ± .048 | .031 ± .046 | .027 ± .047 | .029 ± .043 | .024 ± .043 | .025 ± .041 |
| $c_{233}$ | .013 ± .068 | .013 ± .071 | .013 ± .062 | .015 ± .056 | .012 ± .045 | .012 ± .047 |
| $\epsilon_1$ | .024 ± .053 | .014 ± .030 | .038 ± .082 | .035 ± .087 | .041 ± .066 | .041 ± .066 |
| $\epsilon_2$ | .021 ± .052 | .013 ± .028 | .035 ± .081 | .033 ± .086 | .038 ± .064 | .038 ± .065 |
| $\epsilon_3$ | .007 ± .021 | .005 ± .014 | .008 ± .023 | .006 ± .020 | .008 ± .020 | .008 ± .021 |

B4.4 Model-Space Exploration

Figure 25:
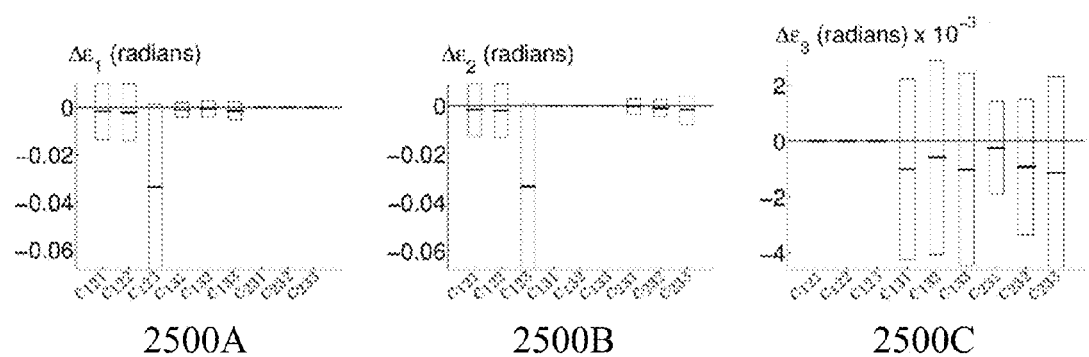
FIG. 25 depicts the individually optimized connection form and the mean errors of fit using the constant Maurer-Cartan embedding as a baseline wherein the boxes illustrate the mean and twice the standard deviation.

We now examine the contribution of each individual connection form in lowering the mean fitting error, by settings all others to zero. As expected, each $c_{ijk}$ only affects the respective $\epsilon_i$ and $\epsilon_j$ errors. FIG. 25 demonstrates that the most important connection form in lowering both $\epsilon_1$ and $\epsilon_2$ is $c_{123}$, since it describes a rotation of the helix angle, which has a large magnitude throughout the volume. $c_{121}$ and $c_{122}$ also significantly lower the error, which supports the use of low dimensional embeddings such as the GHM described in Section B3.1. The smaller contribution of all c13k forms in lowering the fitting error is likely due to the local scale and the isotropic neighborhoods in which the errors were measured, and to the small magnitude of the geometric features that they measure. $\epsilon_3$ reduction is more variable although considerably small because of the stability of the heart wall normal.

The ability of the various Maurer-Cartan embeddings to lower the fitting error using the cardiac frame field can be predicted directly from FIG. 25.

Figure 26:
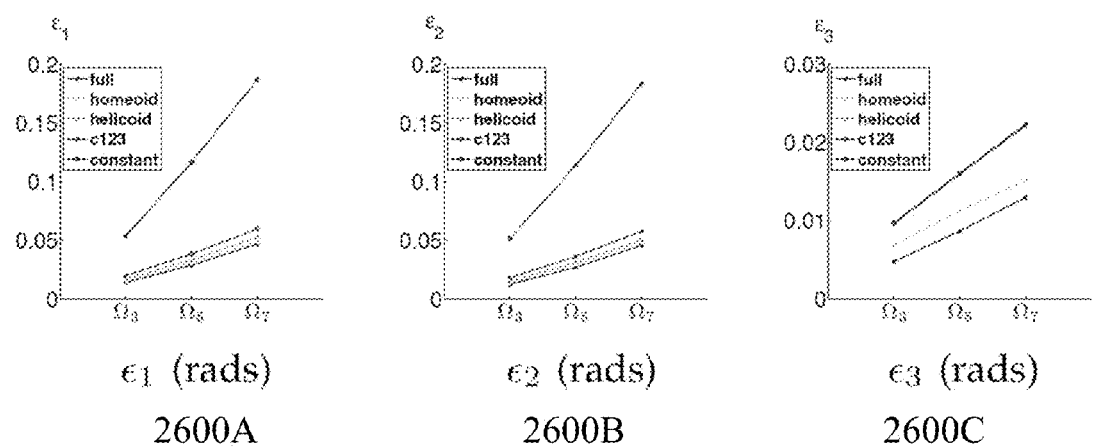
FIG. 26 depicts the mean extrapolation error as a function of neighborhood size for various embeddings.

Embeddings that offer greater complexity in capturing the variation of a particular frame axis will lower the frame error associated with it. FIG. 26 shows the three mean errors $\epsilon_i$ for various embeddings as a function of neighborhood size $\Omega_j$, using optimized computations. In relation to the frame error $\epsilon_1$, all embeddings with an unconstrained $c_{123}$ will perform similarly, as shown in FIG. 26, since it is the connection form that dominates most of the frame field variation. On the other hand, the third frame vector $f_3$ captures the extent to which the principal direction of diffusion remains normal to the heart wall normal. Since fiber directions $u_1$ generally run tangentially to the heart wall, the resulting error is low for all embeddings.

Accordingly, the inventors have shown that measurements of the geometry of cardiac myofibers can be performed using the method of moving frames. These results corroborate and extend existing cardiac literature, most of which have not been reported before. More precisely, the following was observed.

1) Helix Angle: $c_{123}$ measures the rate of change of the helix angle, and is in the order of $-0.290$ rad/voxel. In a 2) Wall Curvatures: $c_{131}$ and $c_{132}$ reflect the sectional curvatures of the heart wall as projected onto the local osculating ellipsoid to $f_1$. Their respective mean values of 0.039 and 0.031 rads/voxel imply radii of curvature of 26 and 32 voxels. These values are in the range of the two principal radii of an aligned ellipsoid to a typical heart in the dataset, which at the mid-region has a circular shape and a half-width of about 25 voxels.

3) Myocyte Fanning: $c_{122}$ and $c_{133}$ are measures of how much cardiac myocytes fan out, and their mean values are 0.015 and $-0.017$ rads/voxel. Based on histological studies, these values are expected to be small, since myocytes form a largely homogeneous, parallel medium.

4) Myocyte Twisting: $c_{123}$, $c_{132}$ and $c_{231}$ are measures of twisting in the collagen matrix that contains cardiac myocytes. Whereas $c_{123}$ corresponds to the variational component of the helix angle, $c_{132}$ describes a turning that is directed in an upward fashion from base to apex, and $c_{231}$ one that rotates the tangent fiber plane.

Accordingly, the inventors have shown that the method of moving frames can be applied to dMRI data and employed to explore and compute the variation of a smooth frame field. The method allows the development of a selection of geometrical embeddings which imposed certain constraints—via thresholding (spherical and ellipsoidal manifolds) or by assuming a functional dependency (e.g. GHM) on connection forms. Although the embodiments of the invention have been presented with respect to simple cases, it would be evident that there are many additional possibilities for developing such embeddings. By carefully tailoring connection form constraints to the application at hand, one can design a powerful geometrical probe. This analysis can be performed whenever smooth flow lines or trajectories need to be interpreted geometrically.

Different embeddings were employed to characterize the geometry of cardiac myocytes. The resulting connection forms relate to established cardiac measurements, many of which were until now only determined from indirect empirical data. These measurements include the rate of change of the helix and transverse angles, measures of cardiomyocyte fanning and twisting, and sectional heart wall curvatures. This research yields new possibilities for differentiation between healthy and pathological cardiac tissue, and for generating models of synthetic cardiac orientations.

C. Tissue Engineering

Heart wall myofibers are arranged in minimal surfaces to optimize organ function. Based upon the analysis performed by the inventors they have established that the orientation of myofibers within the heart are locally arranged in a very special manner which can described by a class of minimal surfaces called generalized helicoids. By describing these surfaces locally with a small number of parameters the inventors have been able to generate mathematical fits to myofiber orientation data measured using diffuse magnetic resonance imaging of rat, dog, and human hearts. The computer model shows how fibers should be oriented locally to give the heart wall its mechanical function, and thus could be used in tissue engineering applications which require the regeneration of heart wall tissue where it has been damaged, as in the case of infarctions. The model can also be used to provide atlases of normal fiber geometry to be used in clinical applications. Previous studies have described the shape of individual fibers as pieces of helical curves, but not their collective volumetric structure in the heart wall.

It would be evident therefore that the computer models of the human heart, for example, can thereby serve as a scaffold for artificial muscle construction. For example, the scaffold may be formed from a polymer using the mathematical model according to embodiments of the invention. Accordingly, implementing a material exploiting polymer fibers aligned and orientated as with a human heart muscle (wall) allows for the construction of a new kind of composite material with flexible, expandable and contractible properties, which could have any number of uses. Further, it would be evident that the models defined according to embodiments of the invention have benefits within heart tissue engineering and the diagnosis of heart muscle diseases.

Whilst the embodiments of the invention described supra have been described with respect to a heart it would be evident that other biological organs and/or elements may be similarly modeled and analysed exploiting data such as diffuse magnetic resonance imaging, for example. Accordingly, the mathematical model may provide the surfaces and orientation of fibers forming the biological structure.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method comprising:
acquiring diffuse magnetic resonance imaging data relating to a heart;
establishing a model relating to the heart based on a generalized helicoid model that expresses a frame field of local fiber directions in a plane tangent to a heart wall;
fitting each data point of the data as a local orthogonal frame expressed as (i, j, k) to represent the local fiber directions from the model; and
determining connection forms $c_{ijk}$ at each data point to represent a rotation of the local orthogonal frame in a spatial neighborhood of the data point in accordance with the data.

2. The method of claim 1, wherein determining connection forms $c_{ijk}$ comprises computing the connection forms $c_{ijk}$ as a minimizer of an energy contained within the spatial neighborhood.

3. The method of claim 2, wherein the energy is solved for using Nelder-Mead iterations.

4. The method of claim 2, wherein determining the connection forms $c_{ijk}$ comprises enforcing bounds on variables used for minimizing the energy.

5. The method of claim 1, wherein at least one of the local fiber directions for the model corresponds to a local normal to the heart wall which is an approximate direction in which an endocardium moves when the heart beats.

6. The method of claim 1, wherein the connection forms $c_{ijk}$ are Maurer-Cartan connection forms.

7. The method of claim 6, wherein (i, j, k) vary from 1 to 3, and wherein $c_{123}$ is related to a rate of change of a helix angle of cardiac fibers within the heart; $c_{131}$ and $c_{132}$ are related to sectional curvatures of a heart wall of the heart; $c_{122}$ and $c_{133}$ are related to a rate of fanning out for cardiac myocytes within the heart; and $c_{123}$, $c_{132}$ and $c_{231}$ are related to measures of twisting in a collagen matrix that contains cardiac myocytes within the heart.

8. The method of claim 1, wherein establishing a model relating to the heart comprises imposing constraints on the local fiber directions to control a shape and complexity of the frame field.

9. The method of claim 1, wherein determining connection forms $c_{ijk}$ at each data point comprises limiting a size of the spatial neighborhood to minimize a fitting error.

10. A non-transitory computer readable medium having stored thereon program instructions executable by a processor for:
acquiring diffuse magnetic resonance imaging data relating to a heart;
establishing a model relating to the heart based on a generalized helicoid model that expresses a frame field of local fiber directions in a plane tangent to a heart wall;
fitting each data point of the data as a local orthogonal frame expressed as (i, j, k) to represent the local fiber directions from the model; and
determining connection forms $c_{ijk}$ at each data point to represent a rotation of the local orthogonal frame in a spatial neighborhood of the data point in accordance with the data.

11. The computer readable medium of claim 10, wherein determining connection forms $c_{ijk}$ comprises computing the connection forms $c_{ijk}$ as a minimizer of an energy contained within the spatial neighborhood.

12. The computer readable medium of claim 11, wherein the energy is solved for using Nelder-Mead iterations.

13. The computer readable medium of claim 11, wherein determining the connection forms $c_{ijk}$ comprises enforcing bounds on variables used for minimizing the energy.

14. The computer readable medium of claim 10, wherein at least one of the local fiber directions for the model corresponds to a local normal to the heart wall which is an approximate direction in which an endocardium moves when the heart beats.

15. The computer readable medium of claim 10, wherein the connection forms $c_{ijk}$ are Maurer-Cartan connection forms.

16. The computer readable medium of claim 15, wherein (i, j, k) vary from 1 to 3, and wherein $c_{123}$ is related to a rate of change of a helix angle of cardiac fibers within the heart; $c_{131}$ and $c_{132}$ are related to sectional curvatures of a heart wall of the heart; $c_{122}$ and $c_{133}$ are related to a rate of fanning out for cardiac myocytes within the heart; and $c_{123}$, $c_{132}$ and $c_{231}$ are related to measures of twisting in a collagen matrix that contains cardiac myocytes within the heart.

17. The computer readable medium of claim 10, wherein establishing a model relating to the heart comprises imposing constraints on the local fiber directions to control a shape and complexity of the frame field.

18. The computer readable medium of claim 10, wherein determining connection forms $c_{ijk}$ at each data point comprises limiting a size of the spatial neighborhood to minimize a fitting error.

\* \* \* \* \*